(12) United States Patent
Zalevsky et al.

(10) Patent No.: US 10,390,729 B2
(45) Date of Patent: *Aug. 27, 2019

(54) METHOD AND SYSTEM FOR NON-INVASIVELY MONITORING BIOLOGICAL OR BIOCHEMICAL PARAMETERS OF INDIVIDUAL

(71) Applicants: BAR ILAN UNIVERSITY, Ramat Gan (IL); UNIVERSITAT DE VALENCIA, Valencia (ES)

(72) Inventors: Zeev Zalevsky, Rosh HaAyin (IL); Javier Garcia, Valencia (ES); Vicente Mico, Valencia (ES); Michael Belkin, Givat Shmuel (IL); Yevgeny Beiderman, Netanya (IL); Israel Margalit, Ramat Gan (IL)

(73) Assignees: Bar Ilan University, Ramat Gan (IL); Universitat de Valencia, Valencia (ES)

( * ) Notice: Subject to any disclaimer, the term of this patent is extended or adjusted under 35 U.S.C. 154(b) by 271 days.

This patent is subject to a terminal disclaimer.

(21) Appl. No.: 15/592,473

(22) Filed: May 11, 2017

(65) Prior Publication Data

US 2018/0110442 A1    Apr. 26, 2018

Related U.S. Application Data

(63) Continuation of application No. 13/564,381, filed on Aug. 1, 2012, now Pat. No. 9,668,672, which is a (Continued)

(51) Int. Cl.
*A61B 5/00* (2006.01)
*A61B 5/08* (2006.01)
(Continued)

(52) U.S. Cl.
CPC .......... *A61B 5/0803* (2013.01); *A61B 3/0008* (2013.01); *A61B 3/102* (2013.01);
(Continued)

(58) Field of Classification Search
CPC . A61B 5/0803; A61B 5/1455; A61B 5/14551; A61B 5/14532; A61B 5/14546;
(Continued)

(56) References Cited

U.S. PATENT DOCUMENTS

RE40,316 E    5/2008 Gobeli et al.
2002/0016533 A1    2/2002 Marchitto et al.
(Continued)

FOREIGN PATENT DOCUMENTS

EP    2156785 A    2/2010
FR    2756047 A1   5/1998
(Continued)

OTHER PUBLICATIONS

Supplemental European Search Report dated Jan. 11, 2018 for European patent application No. EP15743506.
(Continued)

*Primary Examiner* — Eric F Winakur
*Assistant Examiner* — Chu Chuan Liu
(74) *Attorney, Agent, or Firm* — Browdy and Neimark, PLLC

(57) ABSTRACT

A system and method are presented for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility
(Continued)

stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

**8 Claims, 22 Drawing Sheets
(18 of 22 Drawing Sheet(s) Filed in Color)**

Related U.S. Application Data continuation-in-part of application No. PCT/IL2012/050029, filed on Jan. 29, 2012.

(60) Provisional application No. 61/457,718, filed on May 18, 2011, provisional application No. 61/457,202, filed on Jan. 28, 2011.

(51) Int. Cl.

| | |
|---|---|
| A61B 5/145 | (2006.01) |
| A61B 5/1455 | (2006.01) |
| A61B 3/00 | (2006.01) |
| A61B 3/10 | (2006.01) |
| A61B 3/16 | (2006.01) |
| A61B 5/01 | (2006.01) |
| A61B 5/02 | (2006.01) |
| A61B 5/024 | (2006.01) |
| A61B 5/026 | (2006.01) |
| A61B 5/0295 | (2006.01) |
| A61B 5/0205 | (2006.01) |
| A61B 5/0215 | (2006.01) |
| A61B 5/1459 | (2006.01) |
| A61B 5/021 | (2006.01) |

(52) U.S. Cl.
CPC .............. *A61B 3/16* (2013.01); *A61B 5/0066* (2013.01); *A61B 5/0077* (2013.01); *A61B 5/0084* (2013.01); *A61B 5/01* (2013.01); *A61B 5/0205* (2013.01); *A61B 5/0215* (2013.01); *A61B 5/02028* (2013.01); *A61B 5/02035* (2013.01); *A61B 5/0261* (2013.01); *A61B 5/0295* (2013.01); *A61B 5/02416* (2013.01); *A61B 5/0816* (2013.01); *A61B 5/1455* (2013.01); *A61B 5/1459* (2013.01); *A61B 5/14507* (2013.01); *A61B 5/14532* (2013.01); *A61B 5/14542* (2013.01); *A61B 5/14546* (2013.01); *A61B 5/14551* (2013.01); *A61B 5/442* (2013.01); *A61B 5/4504* (2013.01); *A61B 5/4875* (2013.01); *A61B 5/72* (2013.01); *A61B 5/7278* (2013.01); *A61B 3/165* (2013.01); *A61B 5/02133* (2013.01)

(58) Field of Classification Search
CPC ..... A61B 5/0066; A61B 5/01; A61B 5/02028; A61B 5/02416; A61B 5/0261; A61B 5/0295; A61B 5/14507; A61B 5/4875; A61B 5/7278; A61B 5/14542; A61B 5/72; A61B 5/0077; A61B 5/0084; A61B 5/02035; A61B 5/0205; A61B 5/0215; A61B 5/0816; A61B 5/1459; A61B 5/442; A61B 5/4504; A61B 5/02133
See application file for complete search history.

(56) References Cited

U.S. PATENT DOCUMENTS

| | | |
|---|---|---|
| 2002/0049372 A1 | 4/2002 | Diab |
| 2002/0183601 A1 | 12/2002 | Tearney et al. |
| 2003/0209834 A1 | 11/2003 | Hay et al. |
| 2004/0152989 A1 | 8/2004 | Puttappa et al. |
| 2005/0049468 A1 | 3/2005 | Carlson et al. |
| 2006/0025659 A1 | 2/2006 | Kiguchi et al. |
| 2008/0026235 A1 | 10/2008 | Tearney et al. |
| 2009/0209834 A1 | 8/2009 | Fine |
| 2010/0046897 A1 | 2/2010 | Toriya et al. |
| 2011/0013002 A1 | 1/2011 | Thompson et al. |
| 2013/0144137 A1 | 6/2013 | Zalevsky et al. |
| 2014/0020611 A1 | 1/2014 | Sakamoto et al. |

FOREIGN PATENT DOCUMENTS

| | | |
|---|---|---|
| JP | 2006042955 | 2/2006 |
| JP | 2007244533 A | 9/2007 |
| JP | 2010508056 | 3/2010 |
| WO | 2000060350 A2 | 10/2000 |
| WO | 0150955 A1 | 7/2001 |
| WO | 02036015 A1 | 5/2002 |
| WO | 2008053474 | 5/2008 |
| WO | 2008053474 A2 | 5/2008 |
| WO | 2009013738 A1 | 1/2009 |
| WO | 2009151610 A2 | 12/2009 |
| WO | 2010105197 A2 | 9/2010 |
| WO | 2012101644 A2 | 8/2012 |

OTHER PUBLICATIONS

Ponticorvo Adrien et al: "Laser speckle contrast imaging of blood flow in rat retinas using an endoscope" International Society for Optical Engineering, SPIE, vol. 18, No. 9, Sep. 1, 2013, p. 90501.
Youngwoon Choi et al: Scanner-Free and Wide-Field Endoscopic Imaging by Using a Single Multimode Optical Fiber, Physical Review Letters, vol. 109, No. 20, Nov. 12, 2012, pp. 2003901-1.
Ozana Nisan et al: "Demonstration of a Remote Optical Measurement Configuration That Correlates with Breathing, Heart Rate, Pulse Pressure, Blood Coagulation, and Blood Oxygenation", Proceeding of the IEEE, New York, US, vol. 103, No. 2, Feb. 1, 2015, pp. 248-262.
Anand, Arun et al., Speckle-Based Optical Sensor for Low Field Faraday Rotation Measurement, IEEE Sensors Journal, Feb. 2013, vol. 13, No. 2, 723-727.
Shenhav, Asaf et al., Optical sensor for remote estimation of alcohol concentration in blood stream, Optics Communications, Oct. 23, 2012, vol. 289, 149-157—Abstract only attached.
Beiderman, Yevgeny et al., Optical Remote Continuous Sensing of Intraocular Pressure Variations, Proc. of SPIE, 2012, vol. 8209, 820908-1 to 8—Abstract only attached.
Asejczyk-Widlicka, et al., "Fluctuations in intraocular pressure and the potential effect on aberrations of the eye", Br J Ophthalmol ;91:1054-1058 (2007).
De la Torre-Ibarra, et al. "Double-shot depth-resolved displacement field measurement using phase-contrast spectral optical coherence tomography", Opt. Express 14: 9643-9656, (2006).
T. Matsumoto et al., Measurement by holographic interferometry of the deformation of the eye accompanying changes in intraocular pressure Appl. Opt. 17:3538-3539 (1978).
Yevgeny Beiderman et al: "Remote estimation of blood pulse pressure via temporal tracking of reflected secondary speckless pattern" Journal of Biomedical Optics, 15(6):061707-0617077 (2010).
International Search Report for PCT/IL2013/050658, dated Dec. 17, 2013.
Ozana et al "Improved noncontact optical sensor for detection of glucose concentration and indication of dehydration level", Biomedical Optics Express, 5 (6) 1926-1940 (2014).
Koller "A magneto-optical tachometer based on the Faraday effect", Physics Individual Project Siemens-Westinghouse Competition, 1 (Oct. 2000).

(56) References Cited

OTHER PUBLICATIONS

Yu-Lung et al, "A polarimetric glucose sensor using a liquid-crystal polarization modulator driven by a sinusoidal signal", Optics Communications 259 : 40-48, (Jan. 2006).
Jang et al, "Double Lock& Amplifier Faraday Rotation Glucometer" IEEE 26th Annual northeast Bioengineering conference, Storrs, University of Connecticut, 107-108 (Apr. 2000).
Clarke "Development and optimization of an integrated Faraday modulator and compensator design for continuous polarimetric glucose monitoring" (May 2013).
International Search Report, dated Jun. 8, 2015, in corresponding application No. PCT/IL2015050100.

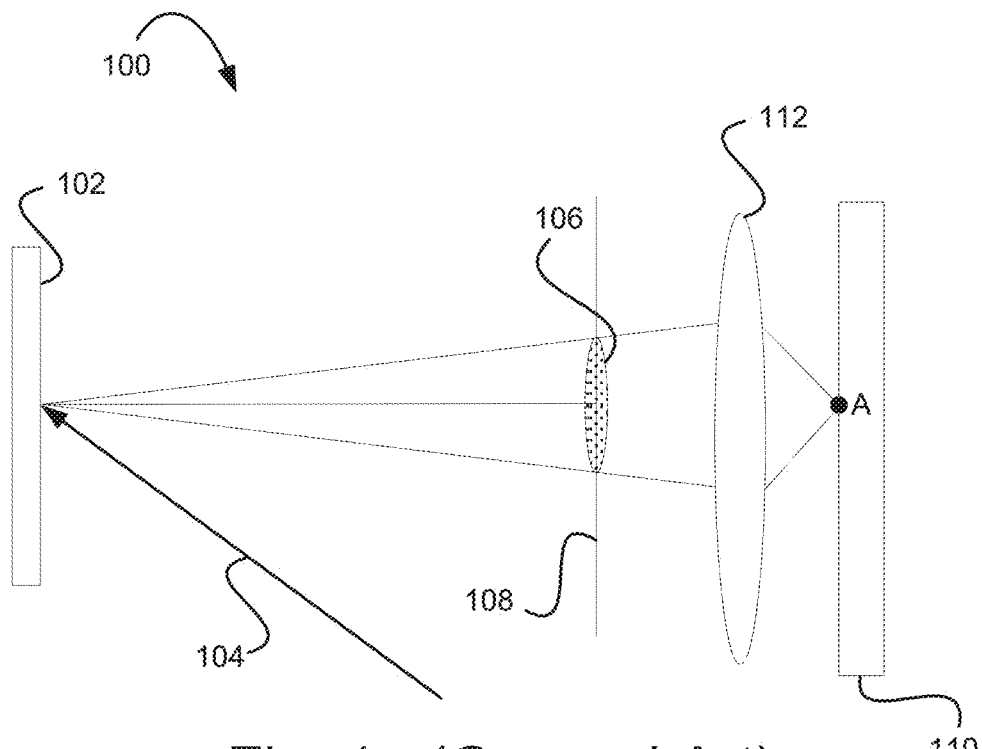
Fig. 1a (General Art)
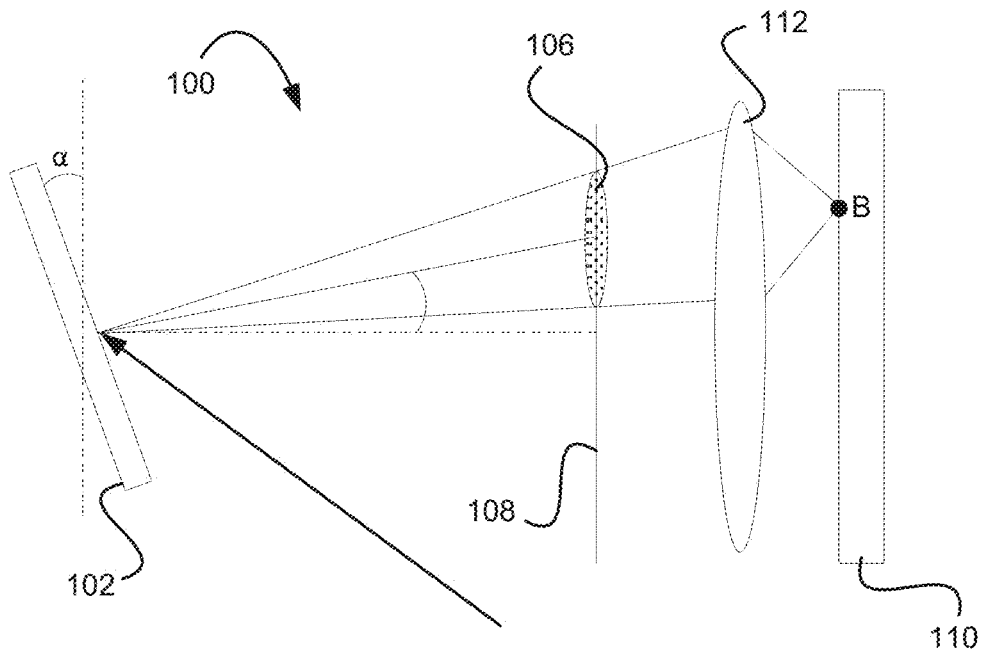
Fig. 1b (General Art)

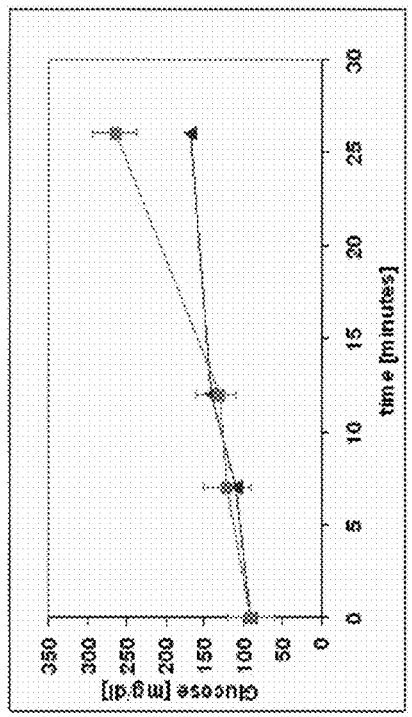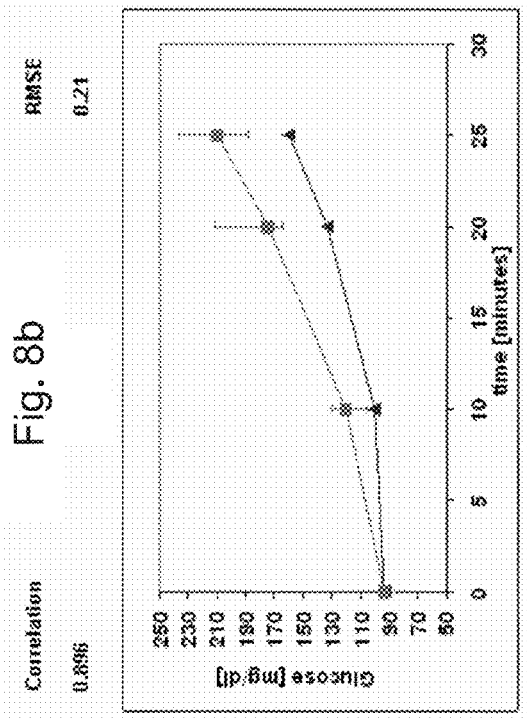

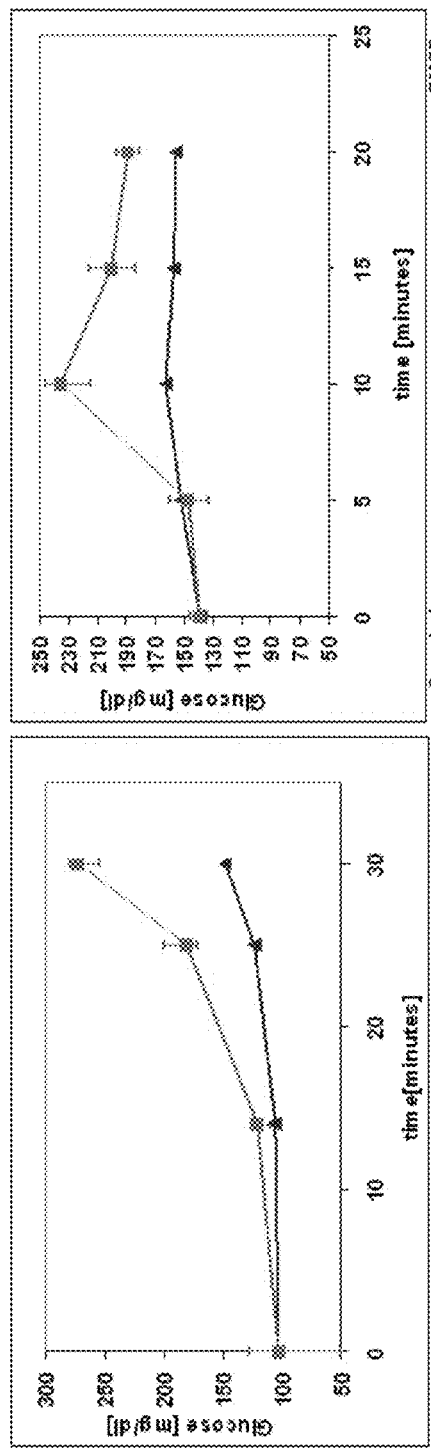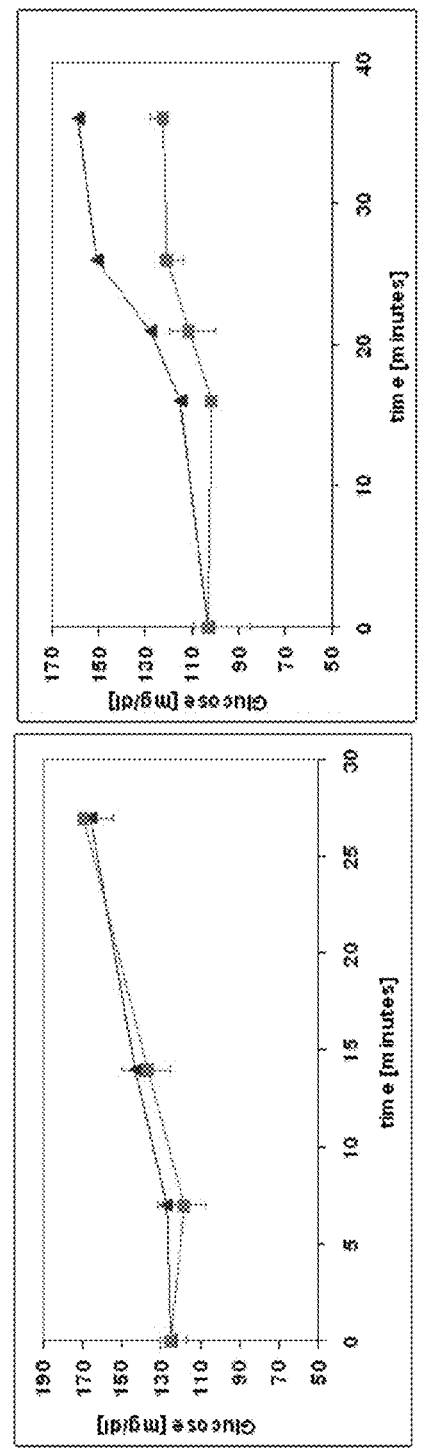
Fig. 10a  Fig. 10b  Fig. 10c  Fig. 10d

METHOD AND SYSTEM FOR NON-INVASIVELY MONITORING BIOLOGICAL OR BIOCHEMICAL PARAMETERS OF INDIVIDUAL

FIELD OF THE INVENTION

This invention relates to a method and system for non-invasively monitoring biological or biochemical parameters and conditions of an individual. The present invention is particularly useful for monitoring biological fluids such as blood.

BACKGROUND

The human body contains many fluids having vital functions within the body. For example, blood flowing in the circulatory system delivers necessary substances such as nutrients and oxygen to cells, and transports metabolic waste products away from those cells. Another fluid is the aqueous humor in the eyes. The aqueous humor maintains the intraocular pressure and inflates the globe of the eye, provides nutrition (e.g. amino acids and glucose) for the avascular ocular tissues, posterior cornea, trabecular meshwork, lens, and anterior vitreous.

Some properties of these bodily fluids are known to be indicative of a condition of the person's body, and determination of such properties may be used in order to monitor a person's health. For example, the blood glucose level (also referred to as blood glucose concentration) being too high or too low can be indicative of a malfunction of the digestive system, such as diabetes mellitus. Blood oxygen level is typically monitored to identify oxygen saturation condition that enables identification of hypoxemia as well allows estimation of hemoglobin in blood. Blood alcohol level (also referred to as blood alcohol concentration) is indicative of alcohol consumption and may be used to determine detrimental effects of alcohol on the gastrointestinal, cardiovascular and central nervous systems. Blood alcohol level is also indicative of impairment in a person's judgment and his ability to perform certain actions, such as driving a vehicle. In the eye, an important property of the aqueous humor is its pressure. This property is commonly called "intraocular pressure". A high intraocular pressure may be indicative of disorders in the eye, such as glaucoma, iritis, and retinal detachment.

In the field of measuring blood-related parameters, such as glucose level and oxygen saturation, many non-invasive techniques have been devised, including impedance-based techniques and optical. For example, in glucose meters based on near infrared spectroscopy, a tissue is illuminated with light in the infrared spectrum, and the light reflected by the tissue and/or the light transmitted through the tissue is measured. The portion of light that is reflected and/or transmitted is indicative of the blood glucose level. Such glucose meters are used for tissue investigation in different depths varying from 1 to 100 millimeters or 10 to 50 micrometers. Some glucose meters use Raman spectroscopy to measure scattered light that has been influenced by the oscillation and rotation caused by glucose. Glucose meters based on photo-acoustic spectroscopy measure parameters of an acoustic pressure wave created by rapid heating of the sampled area. Other glucose meters measure changes in the scattering and the polarization parameters of light caused by glucose. Femtosecond pulse interferometry can be used to determine glucose concentration, by measuring the group refraction index of a glucose solution using a time delay of femtosecond order in a time-of-flight method. Optical coherence tomography can be used to measure and analyze the interference pattern between the coherently backscattered light from specific layers of tissues and a reference beam.

With regard to blood alcohol level, alcohol level is usually examined by determining blood alcohol concentration (BAC) in breath and blood of the affected person. The principle of BAC measurement is based on the fact that alcohol, taken orally, goes into the body system. Equilibrium distribution of alcohol into the different parts of the body mainly liver, kidney, brain, and lungs is attained very rapidly. The ratio of alcohol in the blood to alcohol in alveolar air is approximately 2,100:1 at 34° C., the temperature at which the breath leaves the mouth. Thus, the extent of alcohol intoxication or alcohol consumption is monitored by examining BAC in breath and blood of the affected person, but the obvious choice is blood, an absolute level can be obtained only by drawing a sample of blood. There are several methods for the estimation of BACs using iodometric titrations, breath analyzer, and biosensors.

With regard to intraocular pressure, the most commonly used ophthalmic device for measuring IOP, and current gold standard, is called applanation tonometer known as Goldmann tonometer. It is based on the assumption that the eye is a perfect sphere. Thus, the force required to achieve a fixed degree of applanation (3.06 mm in diameter) when the tonometer head directly applanates the cornea is converted into millimeters of mercury (mmHg) providing the IOP resisting this deformation. Despite of its accuracy and precision, Goldmann tonometry mainly suffers from inter-individual variations due to difference in corneal thickness and rigidity while being an invasive (contact) technique with limitations for monitoring the IOP over time. Note also that this standard method, which involves touching the cornea, also consequently necessitates the use of anesthetic eye drops. As alternative, one can measure the area of applanation when a given constant force is applied to the eye. This can be accomplished, for instance, by blowing from a given distance with a standard blast of air into the eye and measuring the applanation area of the cornea. Using this procedure, the contact in the measurement is avoided but the technique still remains unpractical for monitoring IOP at large periods of time, that is, it fails when identifying peaks and IOP variations.

This single measurement working principle of classical tonometers has encouraged researchers to develop new ways of continuous IOP monitoring. Some examples are the use of sensing contact lenses, some sort of implants with telemetric pressure transducers and devices based on optical principles. The latter is described for example in the following publications: Asejczyk-Widlicka, M., Pierscionek, B. K., *Fluctuations in intraocular pressure and the potential effect on aberrations of the eye*, Br. J. Ophthalmol. 91, 1054-1058, 2007; De la Torre-Ibarra, M. H., Ruiz, P. D., Huntley, J. M., *Double-shot depth-resolved displacement field measurement using phase-contrast spectral optical coherence tomography*, Opt. Express 14, 9643-9656, 2006; Matsumoto, T., Nagata, R., Saishin, M., Matsuda, T., Nakao, S., *Measurement by holographic interferometry of the deformation of the eye accompanying changes in intraocular pressure*, Appl. Opt. 17, 3538-3539, 1978.

GENERAL DESCRIPTION

The present invention aims at providing a novel technique for non-invasively and contactless monitoring one or more conditions of a subject by analyzing image data corresponding to defocused images of secondary speckle pattern responses of the subject varying over time in response to coherent illumination. More specifically, the invention is used for monitoring/measuring parameters/properties of bodily fluids, such as blood, aqueous humor, cerebrospinal fluid in the cranium, and is therefore described below with respect to this specific medical application.

The present invention makes use of the imaging technique disclosed in PCT Patent Publication WO2009/013738 developed by co-inventors of the present application and assigned to the assignee of the present application. This technique is aimed at determining a motion of an object. According to this technique, a coherent speckle pattern propagating from an object is imaged, using an imaging system focused on a plane displaced from the object.

The inventors have now identified that various biological or biochemical conditions of a subject's body affect a motion of the respective body portion. For example, the glucose level and alcohol level in blood affect, inter alia, the viscosity of blood. A change in the blood's viscosity affects the friction between the blood fluid and the vessel walls, and therefore produces a unique vibration profile in the blood vessel and on the skin proximal to the blood vessel. In addition, some of the above mentioned chemicals, such as alcohol, affect the rate and shape of the heart pulsation which can be extracted using the proposed optical technique. The present invention is thus based on the understanding that there is a defined relation between a motion of the body portion (resulting from a motion of a bodily fluid in said portion) and one or more properties of the fluid. The inventors have therefore developed a novel technique that utilizes relations between various parameters, characterizing a change in detected speckle pattern from the body over time, and the body conditions.

According to the invention, speckle pattern is detected over time with a certain sampling rate, and a spatial correlation function between successively sampled frames (images) is determined. The correlation function typically has a Gaussian-like spatial profile and can therefore be described by a "correlation peak" whose temporal variations correspond to a change in the speckle pattern over time. This may be a change in a position (shift) of the speckle pattern in the detector plane causing the change in the spatial position of the correlation peak (the shift of the speckle pattern in time shifts also the obtained spatial correlation peak), and/or a change in the shape or distribution of the speckle pattern causing the change in the correlation peak value. Then, the change in location and/or value of the peak of the spatial correlation function over time (corresponding to the change in the speckle pattern as a result of motion of the corresponding body portion being imaged) is analyzed in accordance with the condition/property to be determined. To this end, the invention utilizes predetermined models, each model presenting a relation between one or more parameters of the time varying spatial correlation function (e.g. the time varying position of the spatial correlation peak or the time varying value of this peak) and a biological or biochemical property/condition of the body. Thus, appropriate one or more parameters of the temporal change in some features of the spatial correlation function (as the temporal change in the position of the peak of the spatial correlation function or in its value) are determined and then the selected model is applied to determine biological or biochemical property/condition.

With reference to blood, the inventors have found that human blood vessels vibrate due to variable (from systolic to diastolic) blood pressure. The human wrist may be one possible spot for blood vessels observation and vibration analysis, especially for heart beat monitoring. As the motion of the blood vessels is a function of blood pressure change, appropriate detection of the blood vessels' movement provides for determining various properties/conditions of the blood, such as those related to blood pressure, namely blood pulse pressure (the difference between the systolic and diastolic pressures), as well as blood flow volume (relative), pulse wave velocity, substance concentration in blood, etc.

A vibration profile of a blood vessel is a unique one. It is characterized by many individual properties, such as vessel elasticity, human fat layer, blood viscosity etc. Therefore any change of one of these properties can distort this profile. For example, the glucose level and alcohol level in blood affect, inter alia, the viscosity of blood. A change in the blood's viscosity affects the friction between the blood fluid and the vessel walls, and therefore produces a unique vibration profile in the blood vessel and on the skin proximal to the blood vessel. In addition, some of the above mentioned chemicals, such as alcohol, affect the rate and shape of the heart pulsation, which can extracted using the proposed optical technique.

Therefore, according to some embodiments of the present invention, there is provided an optical technique to monitor substance concentration/level in blood based on determining and analyzing a change in the speckle pattern over time caused by skin vibrations due to blood flux pulsation. The secondary speckle pattern's spatial correlation function is indicative of the motion of a region of human skin (e.g. skin on the wrist) illuminated by a spot of laser beam, and can be therefore used to determine the substance concentration/level in blood. One or more properties of the blood can be extracted by determining parameters in the time varying characteristics of features in the spatial correlation function of the speckle pattern (features as the position of the correlation peak or its value) generated in response to coherent illumination of the skin portion. For example, the inventors have shown that at least one parameter of the temporal change in the spatial correlation function is in good agreement with the blood glucose level estimated by a conventional measurement technique. Also, the inventors have shown that parameter(s) of the temporal change in the spatial correlation function is in good agreement with blood alcohol level measured by a conventional technique.

With reference to aqueous humor, the inventors have found that intraocular pressure affects the vibration of the eye (e.g. sclera, iris, eye lid), and that a relation exists between intraocular pressure and some parameters of the temporal change in the spatial correlation function of a secondary speckle pattern generated in response to coherent illumination of the eye (the temporal change in the spatial correlation function being indicative of the eye's vibration over time). Therefore, according to some embodiments of the present invention, there is provided a technique for measuring intraocular pressure based on detection and analysis of the temporal change in the spatial correlation function.

According to some further embodiments of the present invention, beams of several wavelengths (generally, at least two wavelengths) may be used to (simultaneously or successively) illuminate the region of interest, and the secondary speckle pattern (and the corresponding time varying spatial correlation function) is determined for each wavelength separately. The time varying spatial correlation function is determined for each wavelength, and a relation between these two or more functions is determined, or a relation (e.g. ratio) between selected parameters of the different time varying spatial correlation functions is determined, as the case may be. More specifically, the time varying spatial correlation function for each wavelength is used (e.g. the change in the position of the spatial correlation peak with time), and the two functions, corresponding to the two different wavelengths are divided one by the other; then the so-obtained time varying ratio is utilized to define the parameter of interest (e.g. the width of peaks, the standard deviation of background noise, etc.), for determination of the blood parameter using one or more appropriate models. This can be useful, for example, in the estimation of blood oxygen level which today is done by pulse oxymetry based on determination of the ratio of transmission of the blood in two predefined wavelengths.

Therefore, according to an aspect of some embodiments of the present invention, there is provided a system for use in monitoring one or more conditions of a subject's body. The system includes a control unit, which includes an input port, a memory utility, and a processor utility. The input port is configured for receiving image data measured by a pixel detector array and being in the form of a sequence of speckle patterns generated by a portion of the subject's body in response to illumination thereof by coherent light according to a certain sampling time pattern. The memory utility is configured for storing one or more predetermined models, the model comprising data indicative of a relation between one or more measurable parameters and one or more conditions of the subject's body. The processor utility configured and operable for carrying out the following: processing the image data and determining a spatial correlation function between successive speckle patterns in the sequence, and determining a time varying spatial correlation function in the form of a time-varying function of at least one feature of the correlation function, the time-varying spatial correlation function being indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

Optionally, the at least one feature of the correlation function comprises at least one of the following: a position of a peak of the correlation unit, and a value of a peak of the correlation function.

In a variant, said one or more body conditions to be monitored comprises blood glucose concentration.

The at least one parameter of the time varying function may comprise at least one of the following: positive pulse amplitude, and ratio between positive and negative peak amplitudes.

In another variant, said one or more body conditions to be monitored comprises blood alcohol concentration.

The at least one parameter of the time varying function may comprise at least one of the following: pulse size, positive pulse size, distance between peak polarities, ratio between main and secondary peak positions, ratio between main and secondary peak amplitudes, and standard deviation of background noise.

In yet another variant, said one or more body conditions to be monitored comprise intra ocular pressure (IOP).

The at least one parameter of the time varying function comprises an amplitude of oscillation.

In yet a further variant, the body condition is blood pulse pressure.

The at least one parameter of the time varying spatial correlation function comprises the amplitude of the main peak (pulse amplitude).

According to a second aspect of some of the embodiments of the present invention, there is provided a system for use in monitoring one or more conditions of a subject's body. The system includes an imaging device and a control unit. The imaging device is configured for imaging a predetermined portion of the subject's body, the imaging device comprising a coherent light source for illuminating said portion of the subject's body with a predetermined number of wavelengths according to a certain sampling time pattern, and a pixel detector array configured and operable for detecting secondary speckle pattern generated by the illuminated portion of the body and generating measured image data indicative of the detected secondary speckle pattern. The control unit is configured and operable for receiving and analyzing said measured image data, the control unit comprising: a memory utility for storing one or more predetermined models, the model comprising data indicative of a relation between one or more measurable parameter and one or more conditions of the subject's body; and a processor utility configured and operable for: processing the image data and determining a spatial correlation function between successive speckle patterns in the sequence, and determining a time varying spatial correlation function in the form of a time-varying function of at least one feature of the correlation function, the time-varying spatial correlation function being indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

According to a further aspect of some embodiments of the present invention, there is provided a method for use in monitoring one or more conditions of a subject's body, the method comprising: providing image data measured by a pixel detector array and being in the form of a sequence of speckle patterns generated by a portion of the subject's body in response to illumination thereof by coherent light according to a certain sampling time pattern; providing one or more predetermined models, the model comprising data indicative of a relation between one or more measurable parameters and one or more conditions of the subject's body; processing the image data and determining a spatial correlation function between successive speckle patterns in the sequence, and determining a time-varying spatial correlation function in the form of a time-varying function of at least one feature of the correlation function, the time-varying spatial correlation function being indicative of a change of the speckle pattern over time; analyzing the time-varying spatial correlation function and selecting at least one parameter of the time-varying function in accordance with one or more body conditions to be determined; and analyzing said at least one selected parameter using one or more of the models to determine one or more corresponding body conditions, and generating output data indicative thereof.

In some embodiments of the present invention, said one or more conditions of a subject's body are associated with one or more properties of at least one bodily fluid.

Optionally, said at least bodily fluid comprises at least one of blood and aqueous humor.

The at least one feature of the correlation function may comprise at least one of the following: a position of a peak of the correlation unit, and a value of a peak of the correlation function.

In a variant, said one or more body conditions to be monitored comprises blood glucose concentration.

The at least one parameter of the time varying function may comprise at least one of the following: positive pulse amplitude, and ratio between positive and negative peak amplitudes.

In another variant, said one or more body conditions to be monitored comprises blood alcohol concentration.

The at least one parameter of the time varying function may comprise at least one of the following: pulse amplitude, positive pulse size, distance between peak polarities, ratio between main and secondary peak positions, ratio between main and secondary peak amplitudes, and standard deviation of background noise.

In a further variant, said one or more body conditions to be monitored comprise intra ocular pressure (IOP).

The at least one parameter of the time varying function may comprise an amplitude of oscillation.

In yet a further variant, the body condition is blood pulse pressure.

The at least one parameter of the time varying spatial correlation function comprises the amplitude of the main peak (pulse amplitude).

BRIEF DESCRIPTION OF THE DRAWINGS

The patent or application file contains at least one drawing executed in color. Copies of this patent or patent application publication with color drawings will be provided by the Office upon request and payment of the necessary fee.

In order to understand the invention and to see how it may be carried out in practice, embodiments will now be described, by way of non-limiting example only, with reference to the accompanying drawings, in which:

FIGS. 1a-1b are schematic drawings illustrating a general art system for measuring motion of an object;

FIGS. 2c-2e exemplify the processing of measured data by the control unit of the system of FIG. 2a;

FIGS. 8a-8d are graphs illustrating the change in a second test subject's blood glucose level and the corresponding change in the amplitude of positive peak (parameter 1 of FIG. 4);

FIGS. 10a-10d are graphs illustrating the change in a fourth test subject's blood glucose level and the corresponding change in the amplitude of positive peak (parameter 1 of FIG. 4);

DETAILED DESCRIPTION OF EMBODIMENTS

Figure 2A:
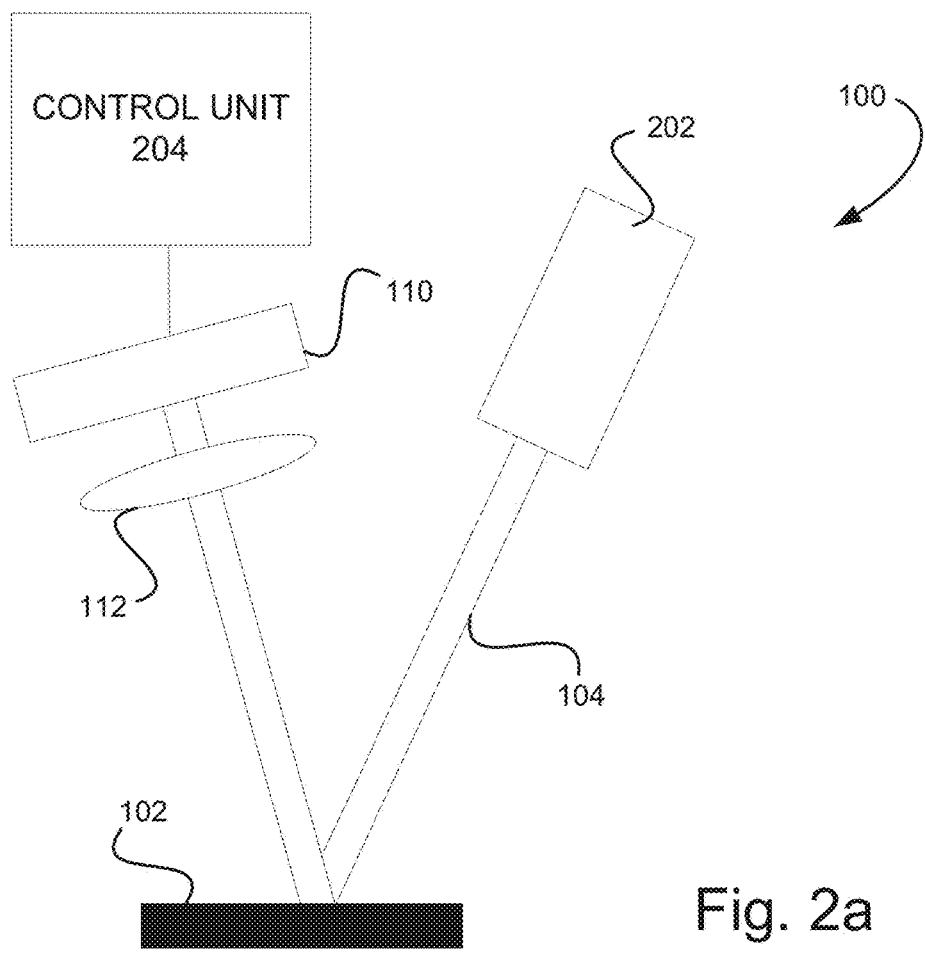
FIGS. 2a-2b are schematic drawings illustrating a system of the present invention for monitoring a subject's condition by measuring one or more biological or biochemical properties of the subject.

Referring now to the drawings, FIGS. 1a-1b are schematic drawings illustrating an imaging system for measuring motion of an object, generally similar to that of the above-indicated PCT Patent Publication WO2009/013738. The system 100 includes an imaging unit, which includes pixel detector array (PDA) 110, and an imaging optics (one or more lenses) 112. The imaging unit is configured for focusing on a plane 108 which is displaced from a plane of an object 102 to be monitored. In other words, the back focal plane of the lens 112 is displaced from the object plane thus producing a defocused image of the object. A coherent light beam 104 (e.g., a laser beam) illuminates an object 102, and a secondary speckle pattern is formed as the reflection/scattering of the coherent light beam 104 from the object 102. The secondary speckle pattern is generated because of the diffusive surface of the object 102. The speckle pattern propagates toward the in-focus plane 108, where it takes a form 106. The speckle pattern propagates in a direction along the optical axis of the system, is collected by the imaging lens 112 and is collected by the PDA 110.

If the object 102 moves in the transverse direction (i.e. into and out of the page, or up and down), the detected speckle pattern changes phase. If the object 102 moves in the axial direction (toward and away from imaging lens 112), the detected speckle pattern changes scale. If the object 102 tilts (as shown in FIG. 1b), then the speckle pattern in the PDA plane shifts position. The scale and shape change as well as the position shift of the speckle pattern are detectable by the PDA, thereby allowing detection of the object's motion along the axial direction and tilting.

With reference to tilting, in FIG. 1a the speckle pattern is detected in the region A of the PDA 110, while in FIG. 1b following the tilt on the object's surface by an angle α, the speckle pattern illuminates and is detected by a region B of the PDA 110. The relative shift of speckle pattern due to the displacement of the object's surface (the object 102) can be estimated as $$\beta = \frac{4\pi \tan \alpha}{\lambda} \approx \frac{4\pi \alpha}{\lambda} \quad (1)$$

where β is proportional to the relative shift δ of the speckle pattern (i.e. the distance between points A and B), α is the tilting angle of object's surface, and λ is the optical wavelength. Assuming that the change in the angle is small enough, a linear proportion is obtained between the relative shift and the angle of tilting.

In light of the above, it can be seen that the object's movement causes changes in properties/profile (phase, magnification, position) of the speckle pattern detected by the PDA 110. Therefore, monitoring a change in the speckle pattern over time is associated with the movement of the object 102 and thus enables detection and characterization of the movement of the object 102.

Figure 2B:
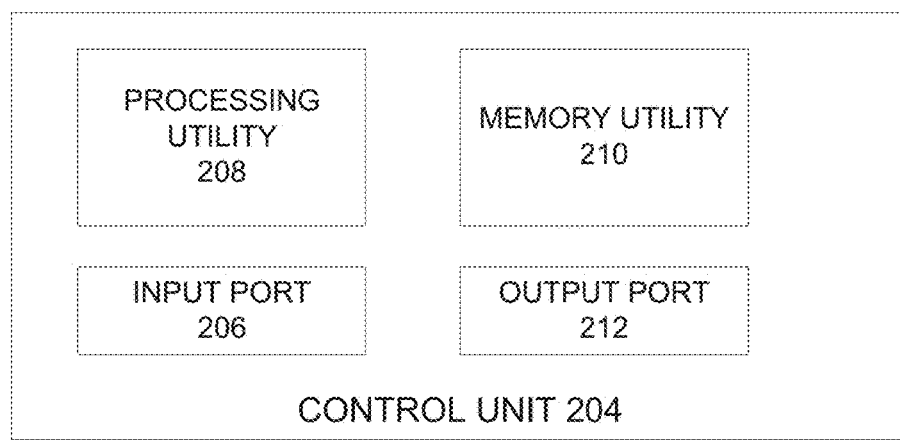

Referring now to FIGS. 2a-2b, schematic drawings illustrate a system 200 of the present invention for monitoring the subject's body condition(s), e.g. measuring at least one property of a bodily fluid. The system 200 includes a source of coherent light 202, an imaging unit having a PDA 110 and an imaging optics (e.g. single lens) 112 as described above, and a control unit 204. The control unit is connectable via wires or wireless signal transmission (e.g. RF, IR, acoustic) to the output of the PDA 110, and in some applications the same or additional control unit may be associated with the light source for selecting appropriate wavelength(s) for illumination.

The source of coherent light 202 emits a light beam 104 to illuminate the object 102 during a certain time period (continuously or by multiple timely separated sessions). The object constitutes a body region of a subject (e.g. individual) whose movement is affected by a change in the body condition, typically a flow of a fluid of interest (i.e. a fluid having a property that is to be measured). The object's diffusive surface responds to coherent illumination by a speckle pattern which propagates toward the imaging optics 112 and is captured by the PDA 110 during said certain time period, to generate output measured data.

Figure 2C:
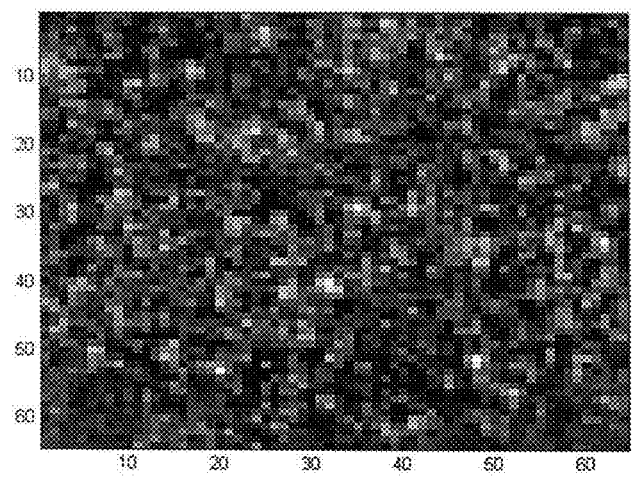
Figure 2D:
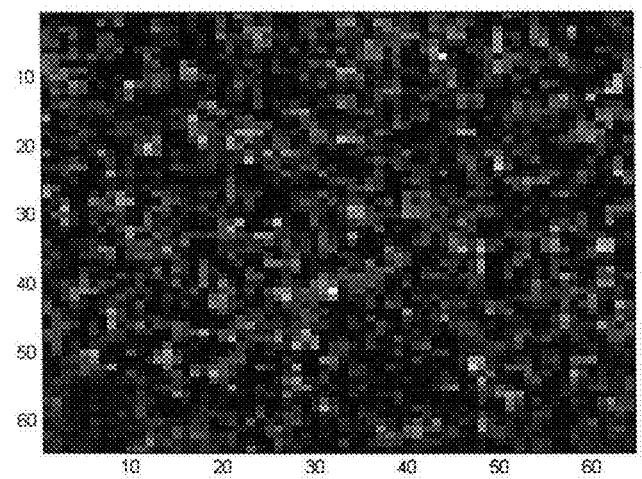
Figure 2E:
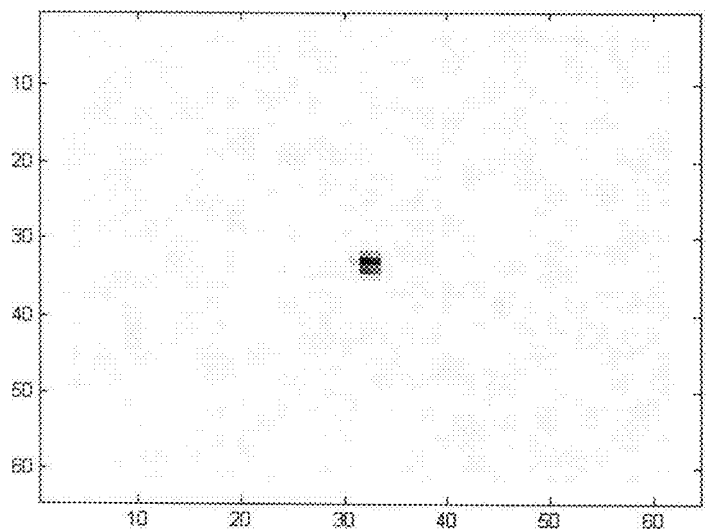

According to the present invention, the control unit 204 receives the measured data (or data indicative thereof and appropriately formatted) from the pixel(s) of the PDA illuminated by the speckle pattern, and processes this measured data to form a spatial correlation function by determining correlation between successive images of the speckle pattern. As exemplified in FIGS. 2c-2e, measured data is in the form of a sequence of speckle patterns generated by the object in response to coherent illumination according to a certain sampling time pattern—two such successively received speckle patterns being shown in FIGS. 2c and 2d. The control unit processes these speckle patterns and determines a correlation function between them, as exemplified in FIG. 2e being in the form of a correlation peak. The black area in FIG. 2e represents the peak of the correlation function between the speckle patterns in FIGS. 2c and 2d.

The control unit 204 is configured for extracting one or more features of the spatial correlation function (e.g. the shift in the correlation peak and/or the change of its value) and monitoring temporal changes of such extracted features, in order to construct data indicative of time variation in the correlation function. The time variation in the correlation function is in turn indicative of variation of the speckle pattern, and therefore of motion in the illuminated body part, which causes such variation in the speckle pattern. Then, from the data indicative of the time variation of the spatial correlation function, one or more parameters are extracted and used for determining one or more conditions of the body.

The optics 112 is slightly defocused with respect to the object's plane. This feature is important in order to convert the tilting movement of the object's surface into transversal movement of the speckles. This provides that the only varying property of the detected speckle pattern, returned from object that undergoes a tilting movement, is its position in the coordinate system of the PDA (i.e. pixel matrix) while other properties (phase and magnification) practically do not change during the tilting of the illuminated object. A time function of the shift of such speckle pattern is tracked by the control unit which operates to apply a certain algorithm to the measured data for correlating the amplitude of the object's motion to the shift in the speckle pattern. In this connection, it should be understood that the speckle pattern shift along the PDA pixel matrix is indicative of the tilting movement of the object with respect to the optical axis, while a change in the scaling (magnification) of the speckle pattern is indicative of the object's motion along the optical axis, and a change in phase of the speckle pattern is indicative of the object's motion substantially perpendicular to the optical axis. The amount of applied defocusing determines the amount of change in each one of the above mentioned properties.

As explained above, the inventors have found that in bodies of humans and animals, one or more properties of a bodily fluid affect the motion of nearby body regions. For example, properties of flowing blood affect the motion of skin on a person's wrist. The pressure of the aqueous humor (i.e. the IOP) affects involuntary vibrations in the eye. The intra cranial pressure affects the motion of the surface of the eardrum. Therefore, the temporal change in the correlation function (as indicated, for example by temporal change of the position and/or value of the obtained correlation function's peak) is indicative of properties (conditions) of the fluid of interest. Therefore, the control unit 204 is configured to perform an analysis of the temporal variations of one or more features of the correlation function (such as the position and/or the value of the correlation peak), caused by time changes of the speckle pattern detected from the object during measurements. From the temporal change in the correlation function analysis, one or more parameters are extracted, these parameters being related to one or more properties of the fluid. The parameters are thus used to determine one or more properties of the fluid.

The control unit 204 includes an input port 206 connected to the PDA 110 and configured for receiving measured data indicative of the detected speckle pattern from the PDA's illuminated pixel(s), a processing utility 208 (software/hardware utility), a memory utility 210, and an output port 212 associated with a data presentation utility or an external storage device, as the case may be. The control unit's processing utility 208 is configured to construct the speckle pattern's spatial correlation function according to the data received from the PDA; the spatial correlation function data may be stored in the memory utility. The processing utility 208 includes appropriate functional modules for determining a spatial correlation function, analyzing the spatial correlation function and extracting one or more features thereof and tracking their variation over time, and constructing data related to the temporal change in the spatial correlation function. Subsequently, the processing utility 208 utilizes a predetermined model (stored in the memory utility) selected for one or more body conditions to be monitored, and analyzes the temporal changes in the object's spatial correlation function according to the selected model. Generally, the model defines one or more sets of parameters (variables) of the temporal changes in the spatial correlation function, the parameters being associated with properties of a certain bodily fluid (e.g., via algorithm or look-up table). Thus, the processor utility 208 analyzes the spatial correlation function and identifies therein the values of one or more of the parameters. Once the parameters are extracted from temporal variations in the spatial correlation function, the processing utility 208 operates for calculating one or more properties of the fluid, according to the selected model.

As will be described more specifically further below, the second set parameters relating to the temporal change in the spatial correlation function may include an average amplitude of a sinusoidal vibration of the temporal change in the correlation function, and/or parameters describing peaks in the temporal change in the correlation function, e.g. the width of the first positive peak.

The output port 212 is configured for transmitting output data from the control unit to one or more output devices (e.g. display, printer, speaker), or to the monitor of the control unit, in order to present data to a user. The output data may include a graph of the temporal changes in the spatial correlation function and/or values of one or more of the extracted parameters, and/or values of one or more properties of the fluid.

As will be explained below, the system 200 may be configured, inter alia, to determine blood-related parameters, such as concentration of substance in blood (e.g. glucose concentration, blood alcohol concentration) and/or oxygen saturation, and/or blood flow volume (relative), blood pulse wave velocity, as well other bodily fluid related parameters such as intra-ocular pressure and/or intra-cranial pressure.

Figure 3:
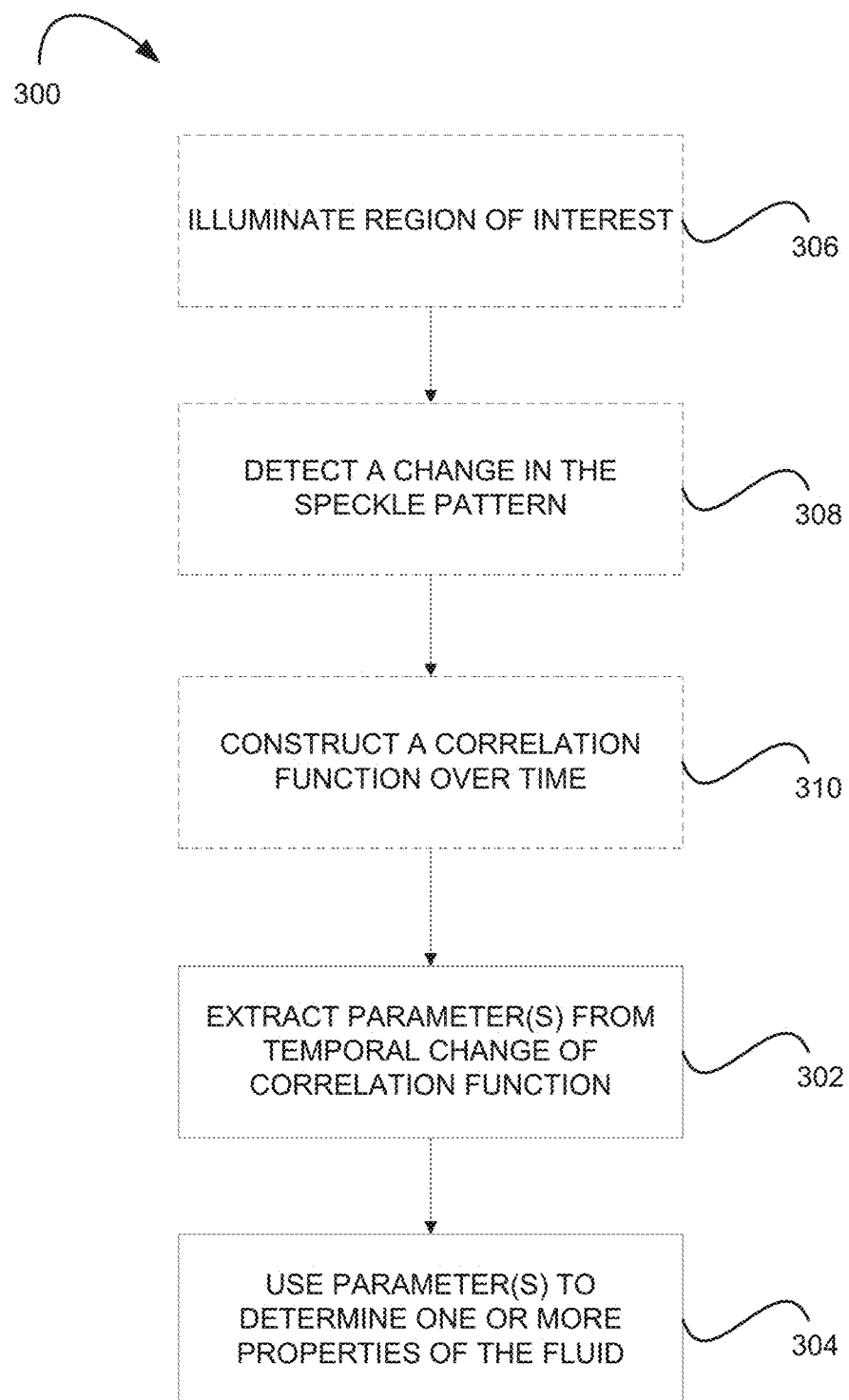
FIG. 3 is a flowchart exemplifying a method of the present invention for monitoring a subject's condition by measuring one or more biological or biochemical properties of the subject.

Reference is now made to FIG. 3, in which a flowchart 300 exemplifies a method of the present invention for measuring a property of a fluid.

At 302, a function indicative of the speckle pattern profile over time is provided and analyzed, in order to extract one or more parameters relating to the temporal shape of the spatial correlation function (as described, for example, by the temporal change in the position of spatial correlation function's peak or the temporal change in the value of this peak), in accordance to the body condition(s) to be monitored. At 304, the extracted parameter(s) is (are) used to determine one or more properties of the bodily fluid according to a predetermined model, and to generate output data indicative of the property of the bodily fluid.

The temporal change in the correlation function may be provided off-line from another processor or storage device, or as exemplified in the figure, may be provided in an on-line mode by processing and analyzing measured data (speckle patterns) from an optical measurement device at 306, 308 and 310. At 306, the region of interest is illuminated by coherent light over a certain time period. At 308, a speckle pattern response to the coherent light is detected, and images of the speckle pattern are recorded over time. Consequently, at 310, the images of the speckle pattern are analyzed to determine one or more characteristics (e.g., position and/or shape) of the speckle pattern. Change in the one or more speckle pattern characteristics is determined between subsequent images, to construct a spatial correlation function of the speckle pattern over the measurement time. One or more features of the spatial correlation function (e.g. a position of the correlation function's peak and/or a value of the correlation function's peak) are extracted and monitored over time, in order to construct data indicative of the temporal change of the spatial correlation function. The so-estimated temporal change in the correlation function can then be analyzed in step 302.

The following are some specific non-limiting examples of the technique of the invention for determining various subject's parameters/conditions.

Blood Glucose Concentration

The following section, describing FIGS. 4-10d, refers to test conducted by the inventors on human subjects, in order to determine a relationship between blood glucose concentration and parameters of the time varying function indicative of the time changes of the speckle pattern caused by vibration of skin on the subjects' wrists (i.e. the temporal change in the spatial correlation function).

The connection between different blood parameters and blood glucose level is explained by:

$$C_v(t) = \frac{(1-\varepsilon) \cdot q_0 \cdot h(t)}{F} \quad (2)$$

where $C_v(t)$ is the venous glucose concentration at time t, F is the blood flow (represents the amount of blood, usually in litters per minute), $q_0$ corresponds to a glucose pulse and represents the amount of glucose (in mg) in the blood (in Kg) per heart beat, ε is the fraction of the glucose pulse that is extracted from the blood system and is metabolized (therefore it will never be recovered at the outlet of the vein), h(t) is the reversible fates of glucose in the organ that causes a delay and a distortion in the appearance of glucose pulse in the vein.

A vibration profile of a blood vessel is a unique one. It is characterized by many individual parameters, such as vessel elasticity, human fat layer, blood viscosity etc. Therefore any change of one of these parameters affects a change of this vibration profile. Changes in glucose level in blood affect the viscosity of blood, while a change in viscosity of blood affects the friction between the blood and the vessel walls, while a change in the friction in turn affects the motion profile. Thus, a change of friction due to a change in glucose concentration in the arteries and veins causes a change of the vibration profile of the vessel. In order to determine glucose concentration from the analysis of the vibration profile of skin on a human wrist, the inventors have analyzed the temporal changes in a spatial correlation function corresponding to the time variations of the speckle pattern in the successive images, by observing quantitative parameters of the temporal changes in a spatial correlation function before and after glucose intake. To be more specific, the temporal changes in the spatial correlation function were in the form of the temporal variations of the spatial correlation function's peak and/or in the temporal variations of the value of the peak of the spatial correlation function. Such parameters were compared to the actual glucose level in the blood that is obtained via a reference measurement with conventional techniques.

about 50 cm. The camera captured images of the secondary speckle pattern from the wrist of the subject at rate of 350 frames per second (fps).

After extracting the speckle pattern in each frame, a spatial correlation between successive frames was performed as described in the above-indicated WO 2009/013738, which is incorporated herein by reference with respect to this specific functional step, to obtain a temporal change of the correlation function indicative of the change in the 2-D position of the speckle pattern's peak versus time.

Figure 4:
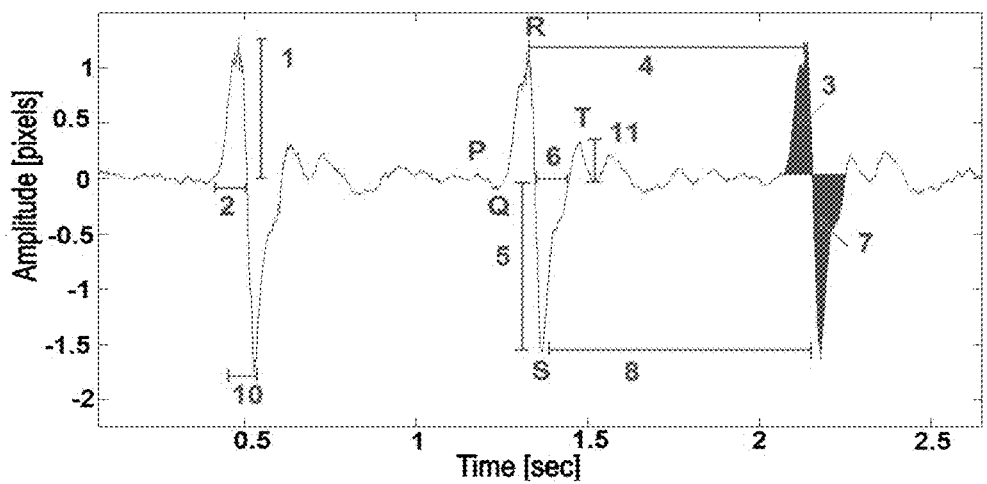
FIG. 4 is a graph exemplifying a function indicative of a time variation of the speckle pattern, as generated by the system of the present invention, and illustrating a plurality of parameters of the function in the time domain that can be used for determining the body conditions.

In FIG. 4, a detected system output with high signal to noise ratio illustrates temporal change in the spatial correlation function indicative of the vibration profile of skin in a human wrist obtained in this experiment. The graph of FIG. 4 includes only several pulses, while in the experiment six pulses were taken into consideration and averaged. It can be seen that every pulse is shaped similarly to electrocardiogram (ECG) PQRST-type pulse. It contains a P pulse, QRS complex, and a T pulse. However, this is a function indicative a mechanical vibration profile, rather than an electrical signal (as ECG), and therefore it corresponds to temporal information about vibration of blood vessels (proximal to the illuminated skin) due to blood flux pulsation.

In the experiment, the following parameters of the temporal change in the position of the peak of the spatial correlation function have been monitored: the main temporal peak amplitude (positive and negative), temporal pulse width (positive and negative), temporal pulse profile energy (positive and negative separately), mean temporal distance between temporal peaks (gap or pulse rate), positive to negative temporal pulse peak ratio, temporal distance from positive to negative temporal peak, secondary temporal peak amplitude and main to secondary temporal peak amplitude ratio. These parameters are listed in Table 1 below, and the reference numerals in Table 1 refer to the numerals present in FIG. 4.

TABLE 1

Parameters of the temporal change in the location of the peak of the spatial correlation function

| N | Parameter | Units | Comments |
|---|---|---|---|
| 1 | Positive pulse amplitude | Pixels | Refers to highest amplitude during one heart beat |
| 2 | Positive pulse width | Seconds | Estimated between 2 zero-crossing points |
| 3 | Positive pulse energy | (Pixels)$^2$ | Integral of the enclosed area in the positive pulse profile |
| 4 | Gap | Seconds | Number of frames between 2 peaks (pulse rate) |
| 5 | Negative pulse amplitude | Pixels | Refers to lowest negative amplitude during one heart beat |
| 6 | Negative pulse width | Seconds | Estimated between 2 zero-crossing points |
| 7 | Negative pulse energy | (Pixels)$^2$ | Integral of the enclosed area in the negative pulse profile |
| 8 | Negative gap | Seconds | Number of frames between 2 negative peaks |
| 9 | Amplitude ratio | — | Absolute value of the ratio between the positive and the negative peaks |
| 10 | Peaks distance | Seconds | Number of frames between the positive and the negative peaks. |
| 11 | Secondary peak amplitude | Pixels | Refers to S point of QRS-complex |
| 12 | Main to secondary peak ratio | — | Absolute ratio between the main and the secondary peaks amplitude. |

An experimental system was constructed similar to the system 200 of FIG. 2a, and used to illuminate a wrist of a subject being fixed by gypsum to allow more accurate measurement. In the experimental system, the source of coherent light was a green laser (having wavelength of 532 nm). The laser output power was about 10 mW. An imaging optics of the camera was slightly defocused. The focal length of the optics that was used in the experiments was 50 mm and the distance from the laser to the subject's hand was In this experiment, several data sets, each indicative of temporal change of the spatial correlation function during a certain sampling period, were obtained by carrying out multiple timely separated sessions, each lasting over a certain time interval including a desired number of detectable pulses, just in order to use average values for the above parameters for each measurement session. The measurement sessions (coherent illumination and speckle pattern detection by pixel matrix) were applied to the same spot on the wrist. Before starting actual measurements, an individual hand template was constructed using gypsum, while a hole was drilled for each one of different subjects to allow the illumination of the subject's wrist. The diameter of the hole was slightly larger than the laser beam's diameter (approximately 1 cm). The test subjects of the experiment were four healthy subjects between the ages of 22 and 35 with different gender and weight. The summary of the subjects' personal information is listed in Table 2. All measurements were repeated several times to assure repeatability and correctness.

TABLE 2

| # | Gender | Age | Weight |
|---|--------|-----|--------|
| 1 | Female | 22 | 55 |
| 2 | Male | 22 | 62 |
| 3 | Female | 24 | 44 |
| 4 | Male | 35 | 90 |

In order to authenticate the required accuracy of 10-15% variation (as per standard glucometer) in the experiment results, the same spot on the wrist was illuminated over time, e.g. by multiple timely separated sessions. To ensure that this requirement was fulfilled, individual fixation devices were built for each subject's hand using gypsum, and several check tests were executed. In the check tests, the arm of each subject was inserted into the fixation device, the spot at which the skin pulsed because of the blood flow was marked, and a hole was drilled through each gypsum in the position of the chosen pulsating spot. Each subject then pulled his/her hand out of the gypsum and re-inserted it. Upon reinsertion, the marked spot was again aligned with the hole.

Figure 5:
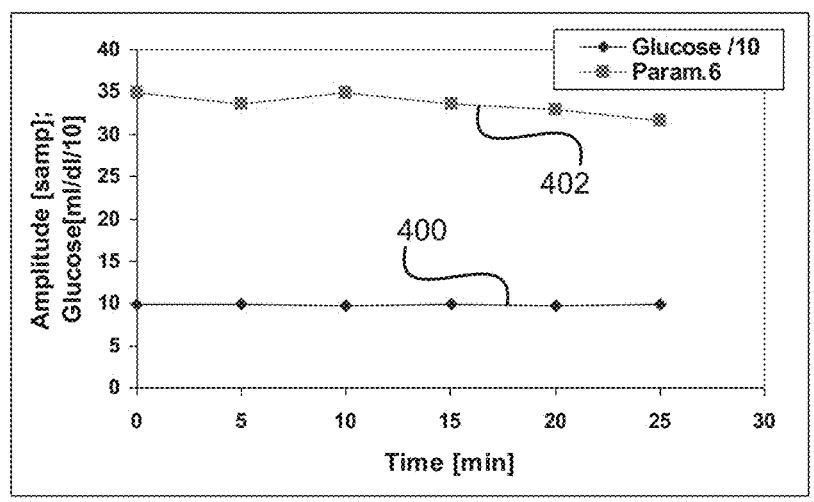
FIG. 5 is a graph which illustrates a test on a subject, in which a substantially constant level of blood glucose concentration was shown to correspond to a substantially constant negative pulse width (parameter 6 of FIG. 4)
Figure 6A:
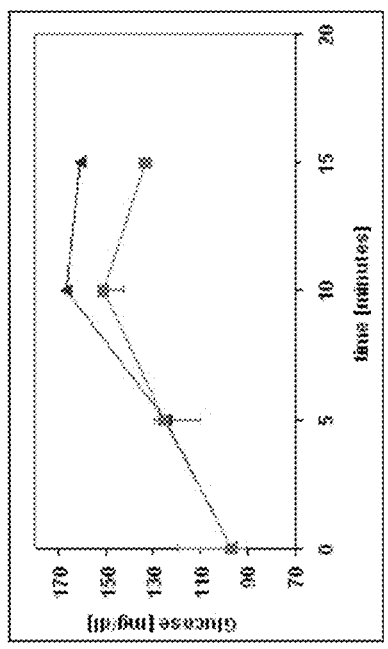
FIGS. 6a-6d are graphs illustrating the change in a test subject's blood glucose level and the corresponding change in the amplitude of positive peak (parameter 1 of FIG. 4)
Figure 6B:
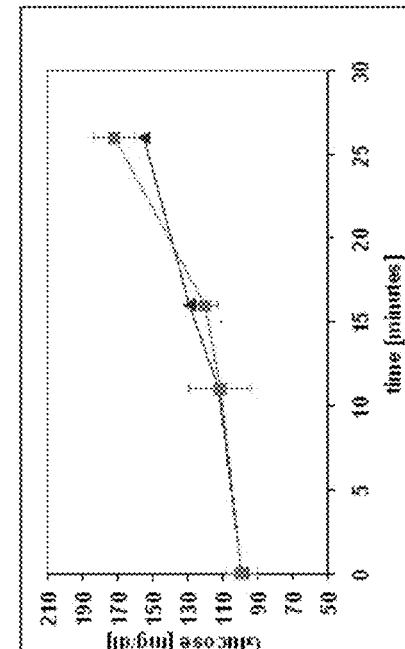
Figure 6C:
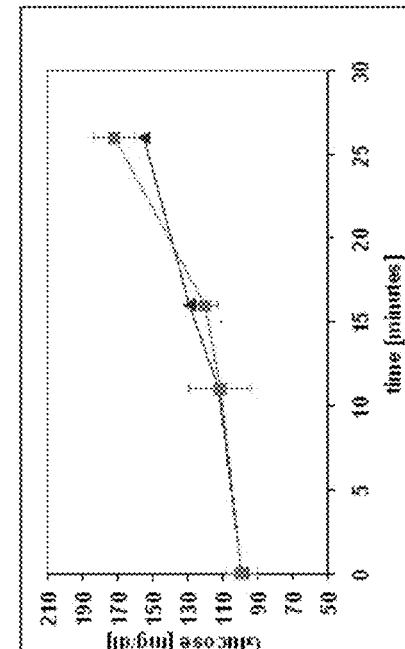
Figure 6D:
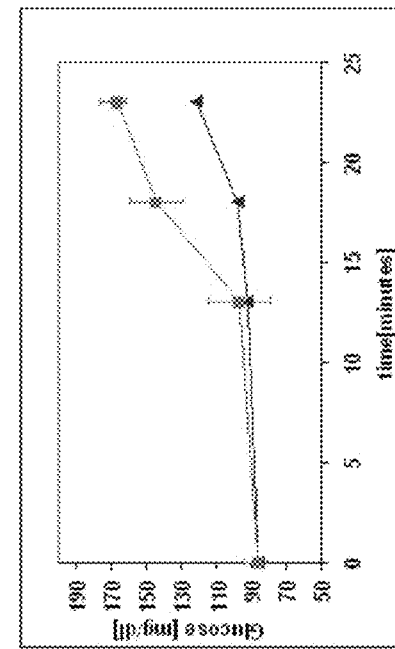

A second check test was aimed to check the stability of the gypsum fixation over time. Each subject inserted his/her hand into the fixation device and stayed fixed for approximately 30 minutes, while he/she was monitored by the system. The result of the second test is illustrated in FIG. 5, where the stability of the system can be clearly seen, since the measured values' results do not vary more than 15%. Substantially constant glucose concentration corresponded to substantially constant negative pulse width (parameter 6 of FIG. 4) of the time variations in the position of the spatial correlation's function peak. Glucose concentration is shown by line 400 in units of [ml/dl] divided by 10 (representing a constant level of 100 [ml/dl]), while the parameter 6 is shown by line 402. The units of parameter 6 are counted in time samples (each sample is 1/rate in time units).

After the preliminary check tests, the actual measurement was performed to relate parameters of the temporal changes in the position of the peak of the spatial correlation function to be indicative of the wrist's temporal pulse profile to glucose concentration in blood. To ensure that the glucose blood level would rise only as consequence of drinking of a sweetened beverage during the experiment, each examined subject preserved a fast for about 12 hours before the measurement took place. The expected values of blood glucose level for non-diabetic person after fasting falls to values range between 90 to 110 [mg/dl]. At the beginning of every experiment it was checked that the subject's blood glucose level was at this range, while later the subject received a sweetened drink and the level was changed.

The rate at which the concentration of glucose increases is different for each individual and depends on many personal parameters, such as body weight, metabolic rate, level of insulin in blood etc. The blood glucose level reached by the test subjects after drinking of about 400 ml of sweetened beverage (40K Cal) was in the range between 150 and 190 [mg/dL]. Each experiment lasted for 50-80 minutes, during it the measurements were carried out repeatedly every 5 minutes. Each 5 minutes sampling included capturing six subsequent video files of the illuminated spot and taking an accurate blood sample with a glucometer ("Accu-check") and manual blood pressure measurement using standard sphygmomanometer. All experiments showed that blood pressure did not change over the time of the experiment. It was important to check that blood pressure remained unchanged, in order to ensure that the expected change in the temporal pulse profile of the position of the speckle pattern's spatial correlation function's peak was indeed caused by glucose intake, rather than by blood pressure change.

A MATLAB program analyzed the videos and extracted the observed parameters from the files. Each file contained about 5 seconds of video samples at rate of 350 fps (frames per second), enabling the construction of data indicative of the temporal variation in position of the speckle pattern's spatial correlation function's peak, usually containing 6 temporal pulse peaks. Each peak was processed separately and the chosen parameters were extracted and averaged, therefore representing the average of approximately 30 peaks of pulse profile per each 5 minutes. For each parameter, the final graph of the estimated glucose level was produced. Joint graphs of the estimated and the reference glucose level for each one of the parameters and for each one of the subjects were created.

In the experiment, only the first samples of the estimated values were taken into account. These samples corresponded to the time period in which the glucose level was rising. These samples were more reliable due to two main reasons. First, glucose metabolism causes changes in biochemical levels of insulinotropic second messengers, including cyclic nucleotides, inositol phosphates, diacylglycerol and $Ca^{2+}$. These changes can also affect blood viscosity. The change in blood fluid viscosity due to biochemistry metabolism is not linear. Second, the test subjects could suffer from "exhaustion". More specifically, although the gypsum was reliable fixation, it was not attached "strongly" enough to the hand, and after approximately half an hour of testing, the subjects could produce spontaneous movement. Such spontaneous movement could have caused a change in the vibration profile not related to the actual glucose change.

The calculation include estimation of a correlation coefficient $C_{fg}$ (which is also called the value of the correlation peak) between optically extracted parameter of the and true glucose concentration obtained via the reference measurement. It is important to mention that this correlation coefficient is not related to correlation function between speckle patterns. Rather, this correlation coefficient is an estimate of the level of correlation between the optically extracted parameter (i.e. the parameter of the temporal change of the spatial correlation function) and the glucose concentration obtained via the reference measurement. A correlation coefficient approaching 1 or −1 is indicative of good correlation between the optically extracted parameter and the glucose concentration. If the correlation coefficient near 0, little or no correlation exists between the optically extracted parameter and the glucose concentration.

For two spatial functions g(x) and f(x) the correlation is defined as:

$$C_{fg}(x)=\int f(x')g^*(x'-x)dx' \quad (3)$$

And for discrete functions:

$$C_{fg}(m\delta x) = \sum_n f(n\delta x) g*(n\delta x - m\delta x) \quad (4)$$

where δx is the spatial sampling interval and m is an integer number. The correlation coefficient or the value of the correlation peak equals to:

$$C_{fg}(0) = \sum_n f(n\delta x) g*(n\delta x) \quad (5)$$

Note that the spatial coordinate is time varying and thus what one actually has is:

$$C_{fg}(x+k(t)) = \int f(x') g*(x'-x-k(t)) dx' \quad (6)$$

where k(t) is a time varying function. For discrete fun $$C_{fg}(m\delta x + k(t)) = \sum_n f(n\delta x) g*(n\delta x - m\delta x - k(t)) \quad (7)$$

The correlation coefficient or the value of the correlation peak equals to:

$$C_{fg}(k(t)) = \sum_n f(n\delta x) g*(n\delta x - k(t)) \quad (8)$$

Furthermore, an estimation of root mean square error (RMSE) was performed to quantify the relation between the reference measurement with conventional glucometer and the measured data obtained by the optical measurements of the invention, where:

$$RMSE = \sqrt{\sum_{i=1}^N \frac{(x_i - r_i)^2}{N}} \quad (9)$$

where $x_i$ is an i-th sample of the parameter values, $r_i$ is an i-th sample of the reference glucose measurements and N is the number of samples. The calculated samples were normalized to have energy of 1, before applying the RMSE estimator in order to obtain the common estimation scale for all parameters.

Dozens of experiments were executed with four test subjects in order to present a proof of principle validation. Initial results show a good correspondence of the estimated parameters with the positive slope of glucose level change in blood. Some of the obtained results are presented in the following figures.

In FIGS. 6a-6d, 7a-7d, 8a-8d, 9a-9d, 10a-10d the temporal evolution of the chosen parameters versus the reference measurement of glucose level taken by glucometer are shown. Glucose concentration in blood is denoted by the lines with triangles and the optically measured parameters from the pulse profile are denoted by the lines with squares. The graph of the reference (glucose level) was obtained by using a conventional glucose meter device ("Acuu-check"). Error bars refer to standard deviation of positive and negative deviations separately, calculated over each 30 peak samples (per each point on the graph). Four different graphs on each figure refer to four different experiments taken with relevant subject on different days, during the morning hours while each subject preserved a fast of 12 hours. Values of the extracted parameters were linearly transformed to glucose level units according to the calibration done per each subject at the first measurement (time 0). Correlation and RMSE coefficients are shown below each graph.

FIGS. 6a-6d are graphs illustrating the change in a test subject's blood glucose level and the corresponding change in the amplitude of positive peak (parameter 1 of FIG. 4). FIGS. 7a-7d are graphs illustrating the change in a test subject's blood glucose level and the corresponding change in the ratio between positive and negative peak amplitudes (parameter 9 of FIG. 4). FIGS. 8a-8d are graphs illustrating the change in a second test subject's blood glucose level and the corresponding change in the amplitude of positive peak (parameter 1 of FIG. 4). FIGS. 9a-9d are graphs illustrating the change in a third test subject's blood glucose level and the corresponding change in the amplitude of positive peak (parameter 1 of FIG. 4). FIGS. 10a-10d are graphs illustrating the change in a fourth test subject's blood glucose level and the corresponding change in the amplitude of positive peak (parameter 1 of FIG. 4).

Figure 7A:
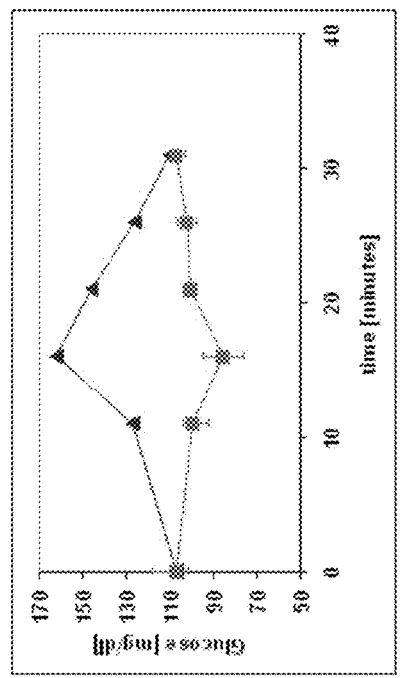
FIGS. 7a-7d are graphs illustrating the change in a test subject's blood glucose level and the corresponding change in the ratio between positive and negative peak (parameter 9 of FIG. 4)
Figure 7B:
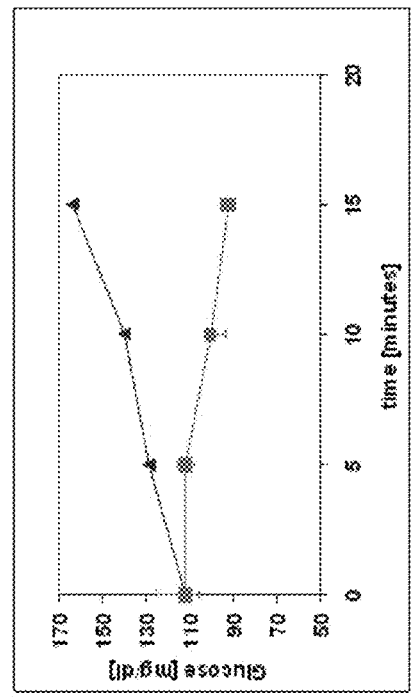
Figure 7C:
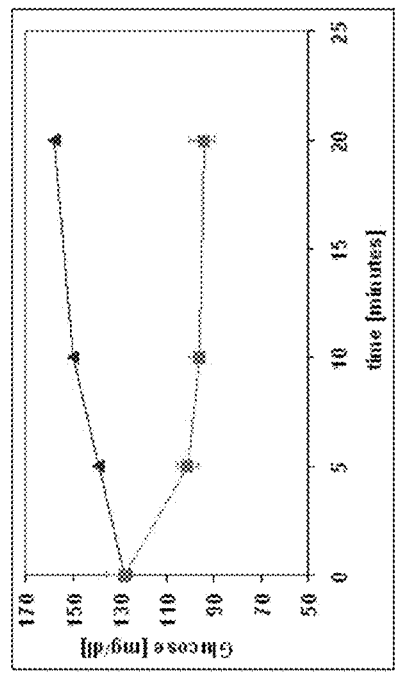
Figure 7D:
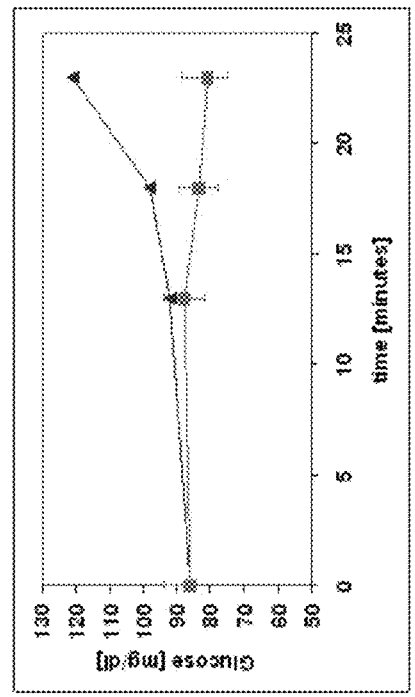
Figure 9A:
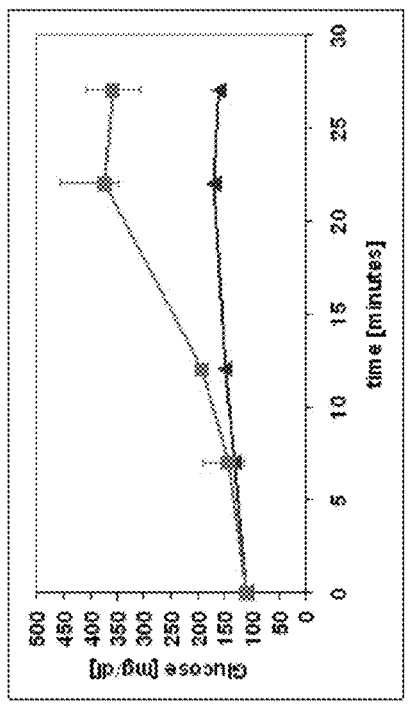
FIGS. 9a-9d are graphs illustrating the change in a third test subject's blood glucose level and the corresponding change in the amplitude of positive peak (parameter 1 of FIG. 4)
Figure 9B:
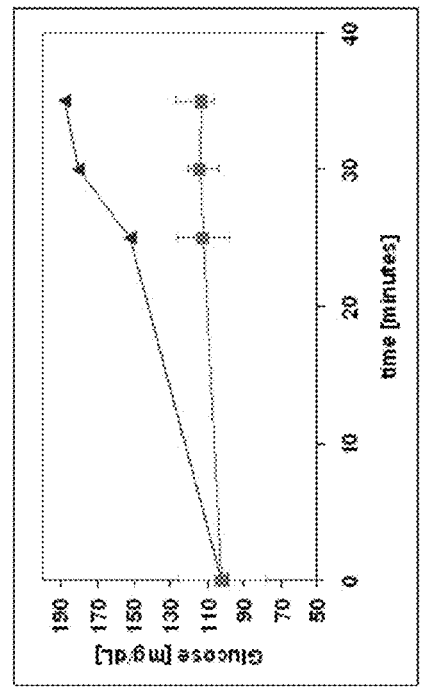
Figure 9C:
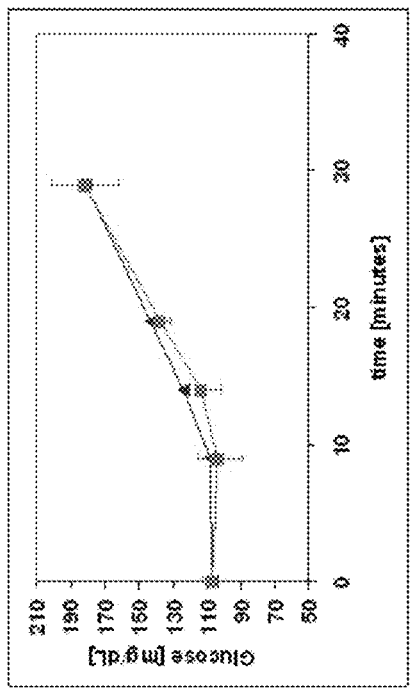
Figure 9D:
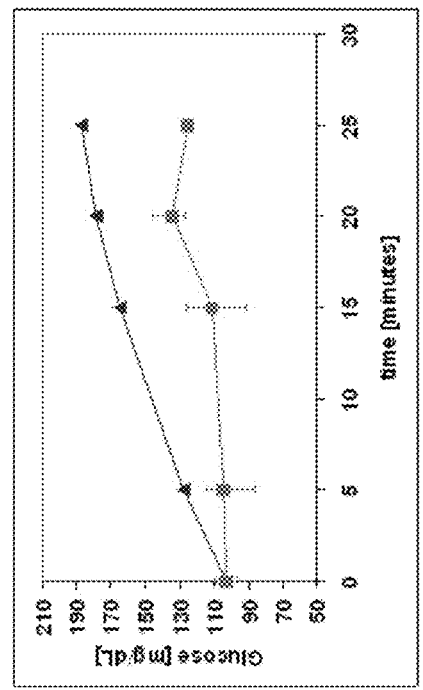

FIGS. 6a-6d refer to subject 1. The best correlative parameter for this subject was parameter 1. FIGS. 7a-7d show an exact inverse ratio between the reference glucose level and the value of parameter 9. Note that parameter 9 is actually a ratio between parameters 1 and 5. Some of the results showed very high correlation with the reference measurement for the full cycle of glucose changes in blood. In FIG. 7b it can be see that parameter 9 tracks the reference glucose level (in opposite direction). The time profile of parameter 9 includes areas in which the slope is positive and areas in which the slope is negative, thereby presenting a full cycle of increase and decrease of glucose level in the blood. A correlation coefficient of –0.916 was obtained between the two curves. RMSE estimator for this parameter was calculated between the inverse function of the normalized estimated parameter (one minus the normalized values) and the reference. RMSE estimator is equal to 0.17 in this case.

FIGS. 8a-8d refer to subject 2. The best correlative parameter for this subject was found to be positive pulse amplitude (parameter 1). FIGS. 9a-9d refer to subject 3. The best correlative parameter for this subject was found to be parameter 1 as well. FIGS. 10a-10d refer to subject 4, with the best correlative parameter 1.

Table 3 summarizes all correlation coefficients, while Table 4 summarizes all RMSE estimator coefficients from the graphs presented in FIGS. 6a-6d, 7a-7d, 8a-8d, 9a-9d, 10a-10d.

TABLE 3

| | Parameter | Test 1 | Test 2 | Test 3 | Test 4 | Average |
|---|---|---|---|---|---|---|
| Subject #1 | Param. #1 | 0.862 | 0.945 | 0.91 | 0.954 | 0.92 |
| | Param. #9 | −0.9 | −0.916 | −0.88 | −0.94 | −0.909 |
| Subject #2 | Param. #1 | 0.984 | 0.896 | 0.966 | 0.99 | 0.959 |
| Subject #3 | Param. #1 | 0.99 | 0.93 | 0.85 | 0.943 | 0.928 |
| Subject #4 | Param. #1 | 0.99 | 0.88 | 0.98 | 0.957 | 0.954 |

TABLE 4

| | Parameter | Test 1 | Test 2 | Test 3 | Test 4 | Average |
|---|---|---|---|---|---|---|
| Subject #1 | Param. #1 | 0.205 | 0.17 | 0.19 | 0.12 | 0.171 |
| | Param. #9 | 0.236 | 0.17 | 0.202 | 0.16 | 0.192 |
| Subject #2 | Param. #1 | 0.083 | 0.21 | 0.18 | 0.08 | 0.138 |
| Subject #3 | Param. #1 | 0.058 | 0.18 | 0.28 | 0.158 | 0.169 |
| Subject #4 | Param. #1 | 0.02 | 0.21 | 0.08 | 0.108 | 0.105 |

Thus, the technique of the present invention has been shown to provide an optical remote configuration for the estimation of glucose concentration in blood. The system of the present invention was tested with clinical trial group and the estimated results show a high correlation and low error comparing to reference measurement obtained by conventional invasive means.

With the technique of the present invention, it was demonstrated that at least one parameter extracted from data indicative of the temporal change of the spatial correlation function between speckle patterns obtained via measurements of speckle patterns generated from the wrist is proportional to the change of glucose concentration in blood. The technique of the present invention provides a non-invasive manner of remote measurement of glucose concentration in blood, while it uses only a low power emitting laser and a camera.

Blood Alcohol Concentration

The following section, describing FIGS. 11a-23, refers to tests conducted by the inventors on human subjects, in order to determine a relationship between blood alcohol concentration and one or more parameters of the temporal changes in a feature (e.g. the correlation peak and/or its value) of the speckle pattern's spatial correlation function in the time domain.

The tests were conducted with an experimental system shown in FIG. 2a. The experimental system included only a green laser to illuminate the inspected object (to generate the secondary reflected speckle) and a defocused camera connected to a computer (control unit) that observes the secondary speckle pattern reflected from the wrist of the subject. The distance from the laser to the subject's wrist was about 10 cm. In all of the experiments, the sampling rate of the camera was 405 FPS (frame per second). The coherent light emitter was a green CW (continuous wave) laser at a wavelength of 532 nm at an approximate power of 100 mW. The laser beam incidence angle was chosen to be 75 degrees relative to the subject's wrist.

During the measurements, each test subject was tested simultaneously by the experimental system and by a conventional alcohol breathing measurement device to get a reliable reference. A BAC calculator was also used to get a secondary reference.

The samples taken during the tests were in the form of an AVI file (video file) that shows the speckles pattern through time. By using 'MATLAB' program with an image processing techniques, the inventors located the position of the 2-D speckles pattern at each frame. The Matlab program first removed background static noise by comparing the adjacent frames, then analyzed the shift in the speckles between adjacent frames to create data indicative of the skin (and therefore vascular) movement.

More specifically, a spatial correlation function between speckle patterns in adjacent frames was determined. Then, the X and Y coordinates of the position of the spatial correlation function's peak were plotted for each frame, and the shift of such peak between adjacent frames was determined, to create a time-varying function indicative of the temporal change of the spatial correlation function, and of the skin (and therefore vascular) movement. The plots were analyzed and several parameters were extracted from the time-varying function. The parameters of the time-varying function included the main peak amplitude, distance between two nearby peaks, ratio between main and secondary peaks amplitude, etc. A total of 19 different parameters were extracted. Every AVI file provided six different temporal pulses and also the average values of the parameters of the six pulses. All this data was plotted as an excel output data table. Each time, five samples of each test were taken and averaged.

This procedure was repeated approximately each 5-7 minutes throughout a period of 35 minutes. Five different experiments were conducted on five subjects. All of the subjects were healthy, average drinkers with average body weight (four males and one female). The first measurement was at time zero, before starting drinking alcohol. Thereafter, the subjects drank known amounts of highly alcoholic beverage and the subjects' vascular behavior was examined. Every measurement by the experimental setup was followed by a breath test, to be used as a reference.

In a second battery of tests, five subjects were tested for a long duration (75 min when taking samples every 15 minutes).

Throughout the duration of the each experiment, each of the subjects was seated in front of the experimental system, while his wrist was illuminated by the laser beam. The arm of each test subject was tied and fixed to the system, in order to ensure that the subject's pulse would not be affected by any other external variables (such as involuntary movement) and thereby to increase of the accuracy of the measurements.

Figure 11A:
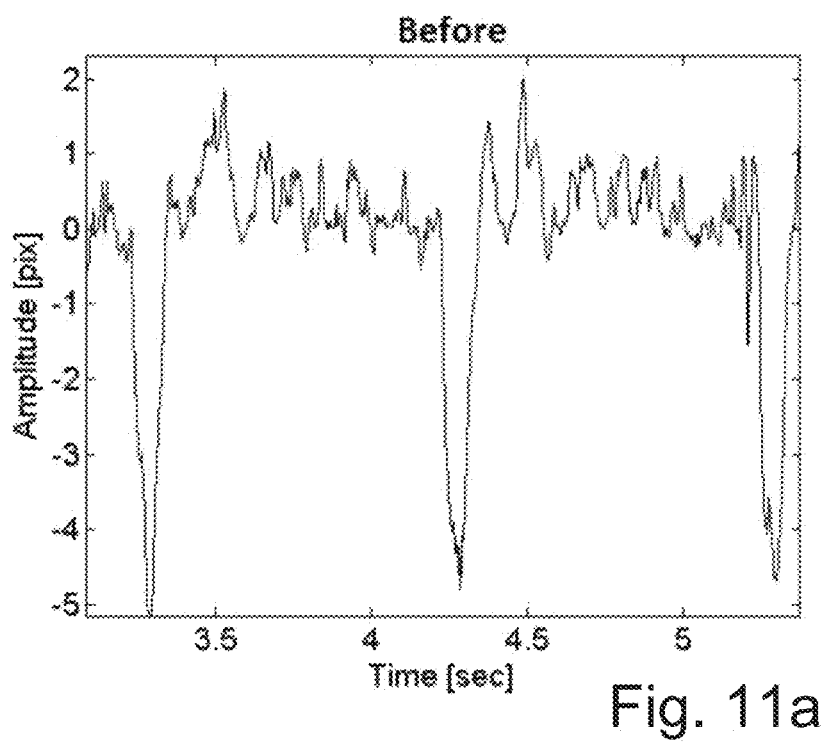
FIGS. 11a-11b are graphs illustrating different functions indicative of a change in the speckle pattern over time generated by the system of the present invention, based on measurements before and after alcohol consumption.
Figure 11B:
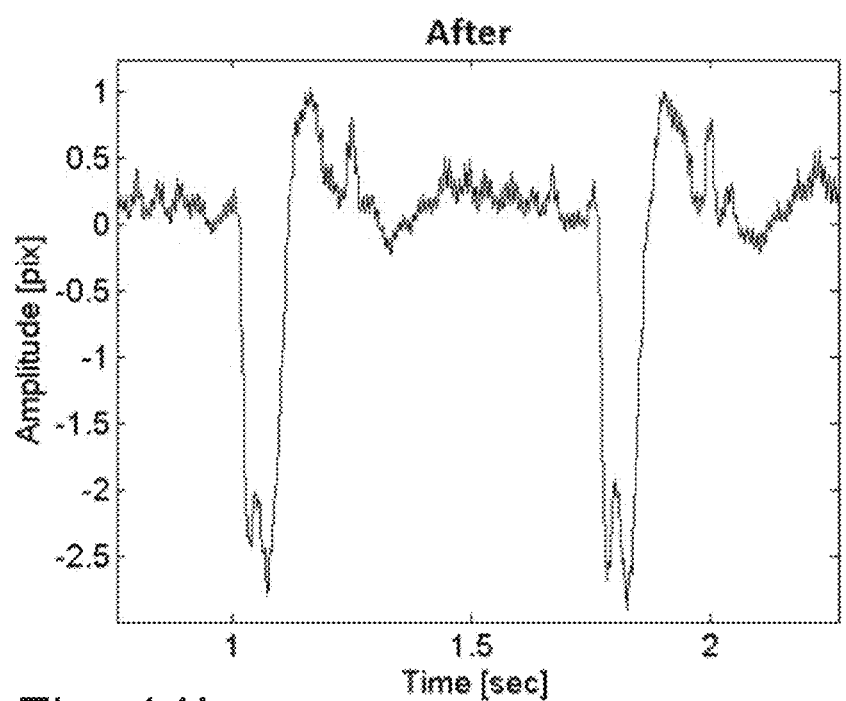

Referring to FIGS. 11a-11b, there are shown different time-varying functions indicative of time changes in the position of the speckle pattern (due to a motion of skin on a human wrist) as generated by the system of the present invention, based on measurements before alcohol consumption (FIG. 11a) and after alcohol consumption (FIG. 11b).

After collecting and analyzing all the results, five parameters which were the most relevant to the experiment were selected. According to scientific studies, alcohol takes time to be absorbed (unlike other materials, like glucose, for example). It was therefore decided that a suitable manner to examine the result is by two time settings: before the alcohol consumption and after half an hour. This is because, according to scientific studies, the maximum alcohol level is reached between half an hour to hour following the ingestion of alcohol. Thereafter, the alcohol level decreases. The selected parameters were: Pulse size, Negative pulse size, peak distance (Peakdis), ratio between main and secondary peak positions (Ratio wid), and ratio between main and secondary peak amplitudes (Main sec peak ratio). These parameters will be illustrated in the figures below. Another test was used as a reference, to measure the parameters of subjects that did not consume alcohol at all. Table 5 shows the relevant details about the test subjects.

TABLE 5

| | Age | Gender | Weight | Alcohol consumption in the experiment [ml] | BAC |
|---|---|---|---|---|---|
| subject 1 | 28 | Male | 75 | 80 | 0.0524 |
| subject 2 | 28 | Male | 61 | 80 | 0.0644 |
| subject 3 | 21 | Male | 82 | 160 | 0.0958 |
| subject 4 | 21 | Male | 78 | 160 | 0.1008 |
| subject 5 | 25 | Male | 70 | 160 | 0.1123 |

Figure 12:
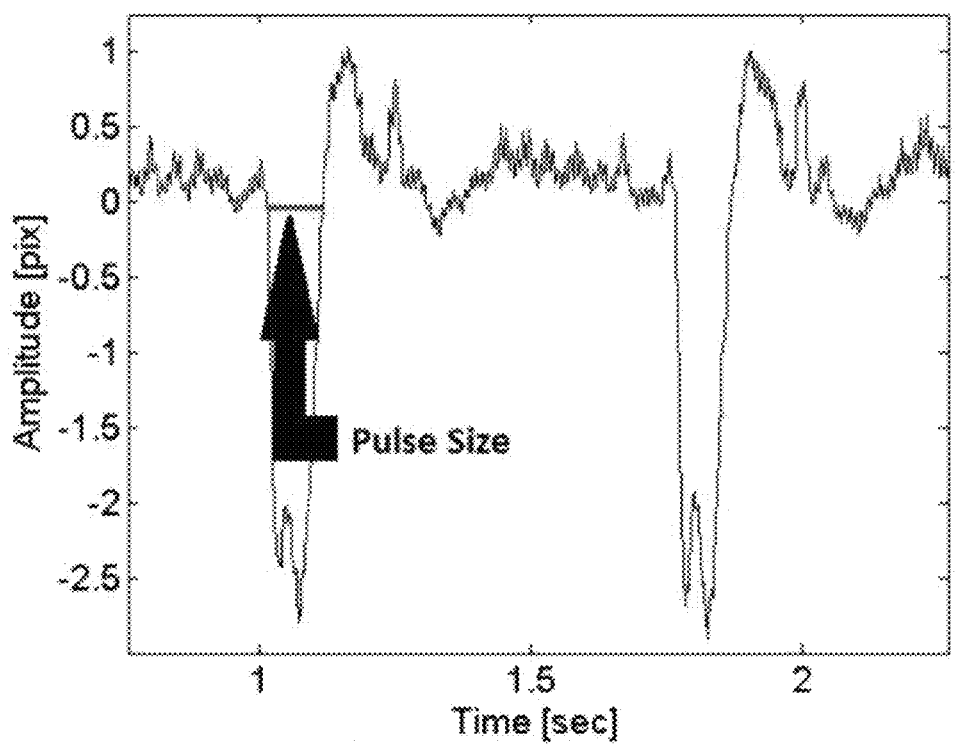
FIG. 12 is a graph illustrating the pulse size (width) of the function indicative of skin vibration.
Figure 13A:
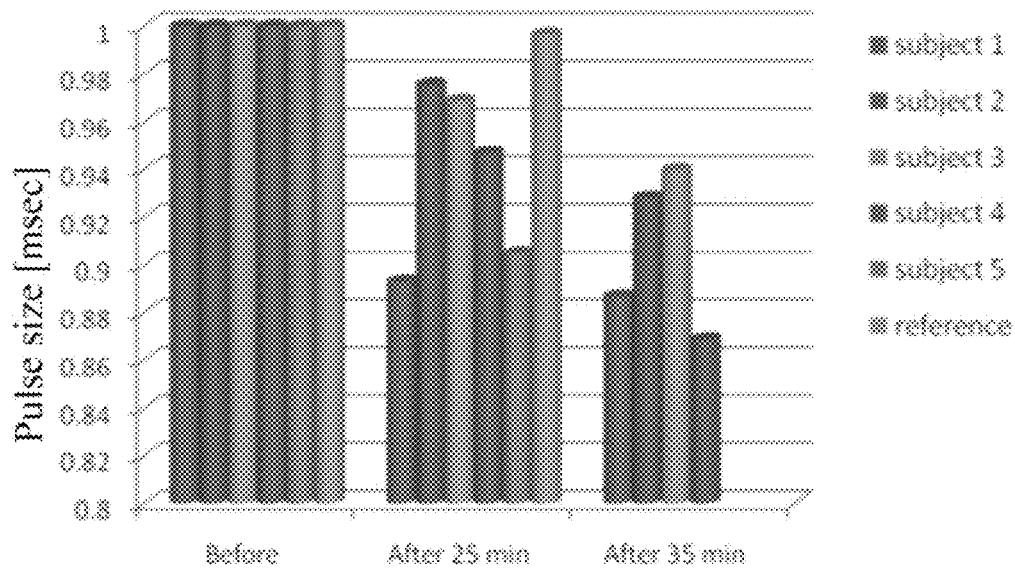
FIGS. 13a-13b are graphs illustrating the change of test subjects' pulse sizes over time, as a consequence of alcohol consumption.
Figure 13B:
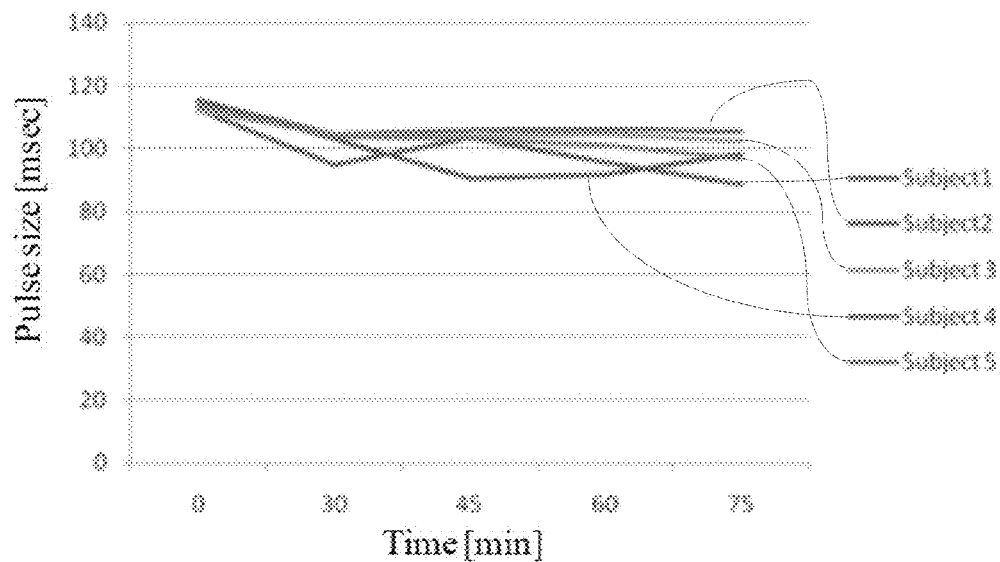

Referring to FIG. 12, the pulse size in a function describing temporal changes in the position of the peak of the spatial correlation function (is the function being indicative of the skin vibration profile in the time domain) is illustrated. FIGS. 13a-13b are graphs illustrating the change of test subjects' pulse sizes over time, as a consequence of alcohol consumption.

The pulse size is the width of the main pulse at the level at which the shift's amplitude is zero. The units of this parameter are milliseconds. The pulse size is the amount of time that the outer layers of the blood vessels are subjected to the largest shift.

Table 6 summarizes values the of pulse size before drinking alcohol and after significant time (25 min & 35 min). Table 7 summarizes the values of the pulse size in the long duration test, where measurements were taken before drinking alcohol and every 15 min thereafter (for 75 min).

TABLE 6

|  | Before | After 25 min | After 35 min |
| --- | --- | --- | --- |
| subject 1 | 121.481 | 108.477 | 107.737 |
| subject 2 | 102.551 | 100.049 | 95.185 |
| subject 3 | 116.049 | 112.428 | 109.053 |
| subject 4 | 135.852 | 128.642 | 118.025 |
| subject 5 | 109.037 | 98.663 | — |
| reference | 111.501 | 111.111 |  |

TABLE 7

|  | 0 | 30 min | 45 min | 60 min | 75 min |
| --- | --- | --- | --- | --- | --- |
| subject 1 | 112.4848 | 94.66667 | 103.4921 | 95.7193 | 88.5614 |
| subject 2 | 115.0222 | 104.7111 | 105.6667 | 106.2667 | 105.2222 |
| subject 3 | 112 | 104.475 | 103.6875 | 104.4231 | 102.2 |
| subject 4 | 115.4211 | 103.0909 | 90.63158 | 91.58824 | 98.5 |
| subject 5 | 113.4868 | 103.6364 | 103.125 | 101.25 | 96.90789 |

The data of tables 6 and 7 is shown graphically in FIGS. 13a and 13b, respectively.

It can be seen see that there is constant and prominently visible decrease in the pulse duration, that shows "sharper" (shorter) movement of the pulse. This decrease in the pulse duration can be indicative of a high blood alcohol concentration.

Figure 14:
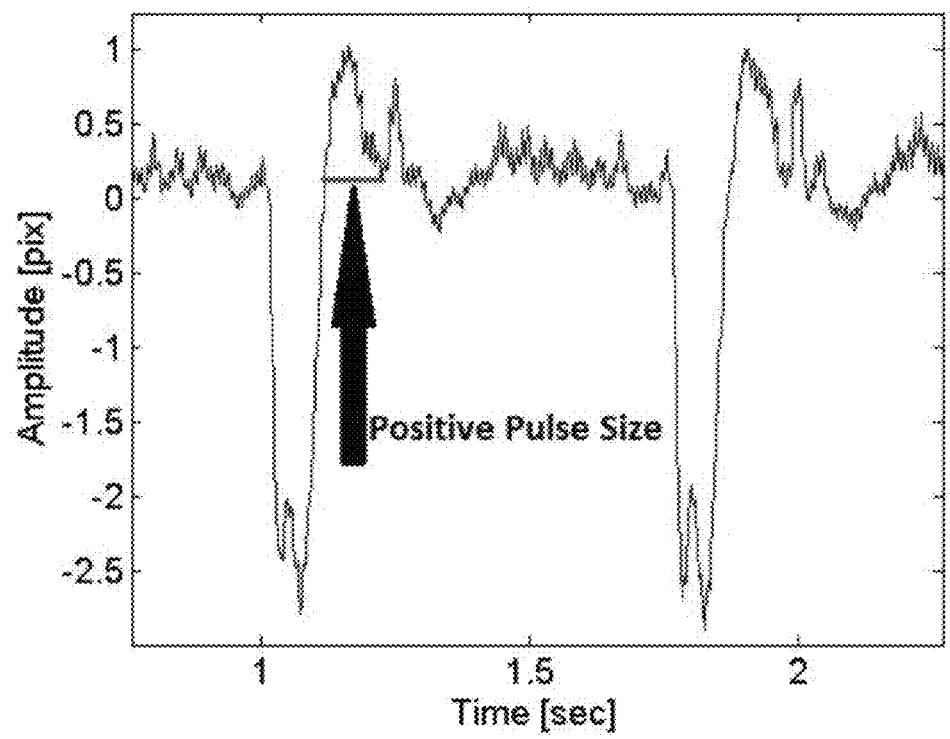
FIG. 14 is a graph illustrating the positive pulse size of the function indicative of skin vibration profile in the time domain.
Figure 15A:
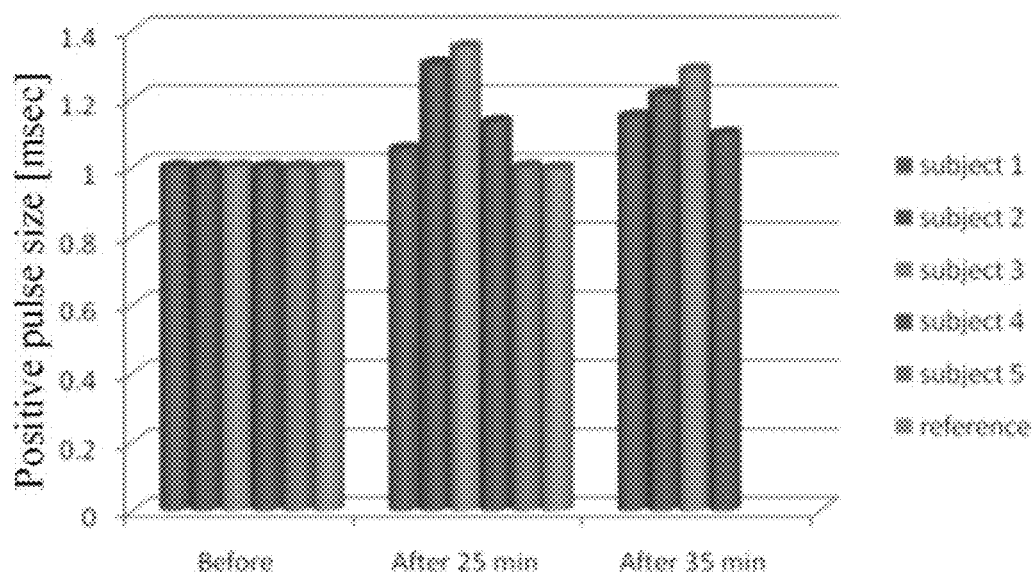
FIGS. 15a-15b are graphs illustrating the change of test subjects' positive pulse sizes over time, as a consequence of alcohol consumption.
Figure 15B:
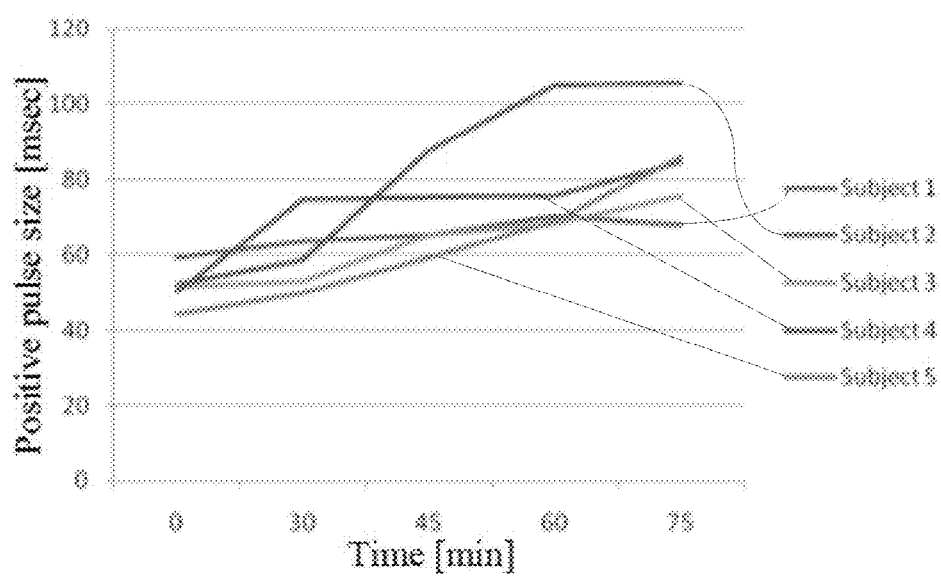

Referring to FIG. 14, the positive pulse size in a function describing the temporal variations in the position of the spatial correlation function's peak is illustrated. FIGS. 15a-15b are graphs illustrating the change of test subjects' positive pulse sizes over time, as a consequence of alcohol consumption.

The positive pulse size is the width of the positive pulse (relative to the main peak) at the level at which the shift's amplitude is zero. The units of this parameter are milliseconds.

Table 8 summarizes values the of positive pulse size before drinking alcohol and after significant time (25 min & 35 min). Table 9 summarizes the values of the pulse size in the long duration test, where measurements were taken before drinking alcohol and every 15 min thereafter (for 75 min).

TABLE 8

|  | Before | After 25 min | After 35 min |
| --- | --- | --- | --- |
| subject 1 | 167.737 | 176.675 | 192.428 |
| subject 2 | 148.189 | 192.741 | 179.704 |
| subject 3 | 134.140 | 181.152 | 172.016 |
| subject 4 | 84.864 | 99.827 | 99.580 |
| subject 5 | 104.938 | 118.765 | 115.136 |
| reference | 158.951 | 152.910 |  |

TABLE 9

|  | 0 | 30 min | 45 min | 60 min | 75 min |
| --- | --- | --- | --- | --- | --- |
| subject 1 | 52.13333 | 58.66667 | 87.53846 | 104.9333 | 105.7143 |
| subject 2 | 59.07692 | 63.54545 | 65.40741 | 70.18182 | 67.90476 |
| subject 3 | 51.42857 | 52.92308 | 65.14286 | 68.34783 | 75.46667 |
| subject 4 | 50.36364 | 74.66667 | 75.17647 | 75.47368 | 84.5 |
| subject 5 | 44.2 | 50 | 59.15789 | 68.76923 | 85.89474 |

The data of tables 8 and 9 is shown graphically in FIGS. 15a and 15b, respectively.

It can be seen that there is constant and prominently visible increase in the pulse duration. This shows "dull" movement of the positive pulse, a behavior opposite to that of the main pulse.

Figure 16:
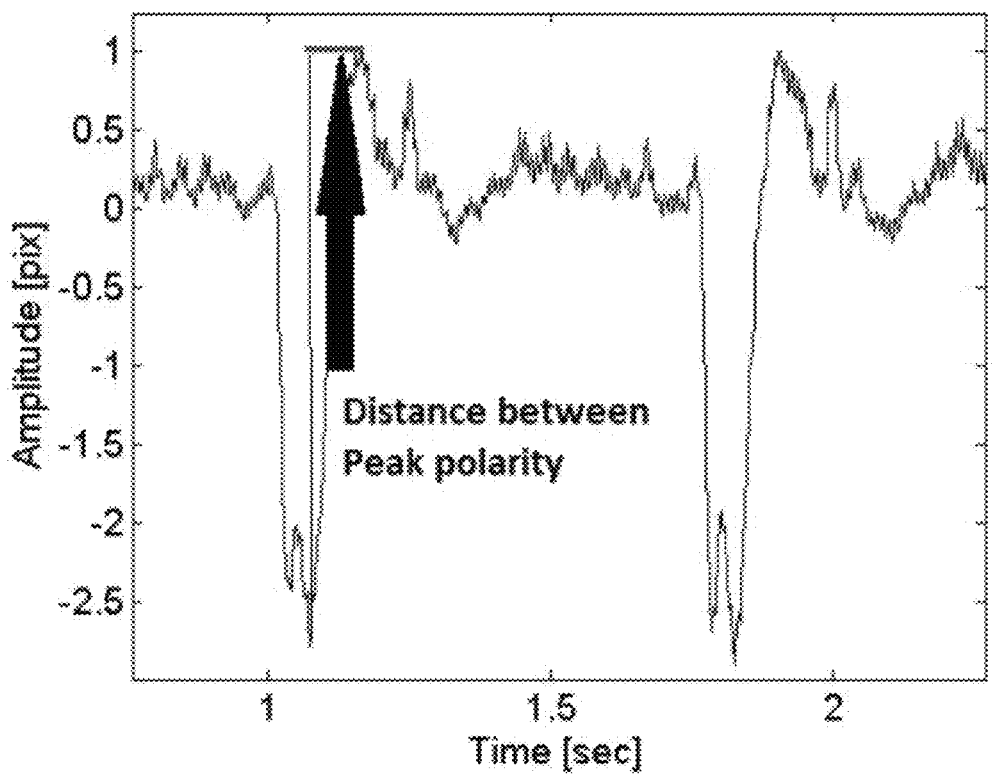
FIG. 16 is a graph illustrating the distance between peak polarities of the function indicative of skin vibration profile in the time domain.
Figure 17A:
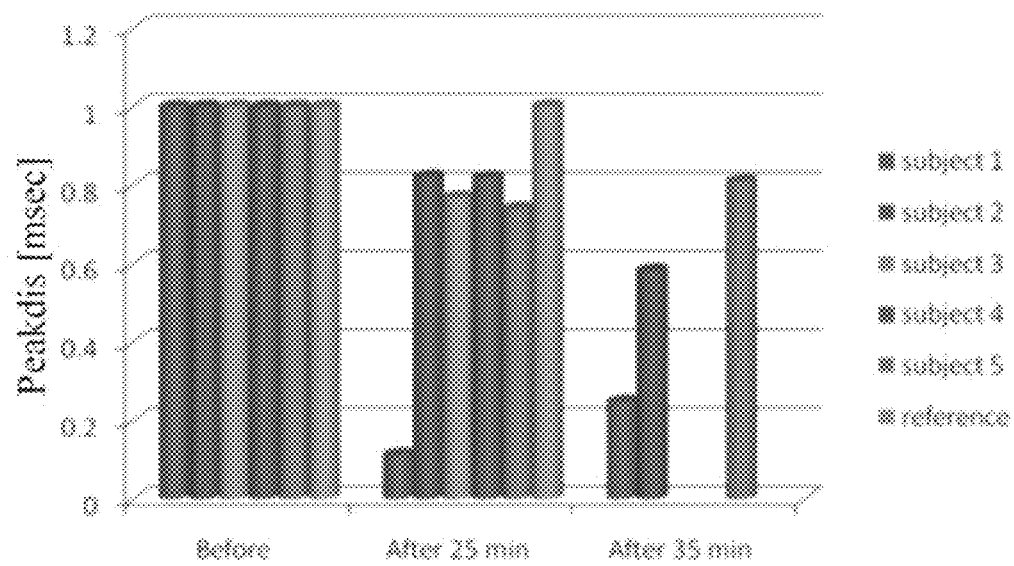
FIGS. 17a-17b are graphs illustrating the change of test subjects' distances between peak polarities over time, as a consequence of alcohol consumption.
Figure 17B:
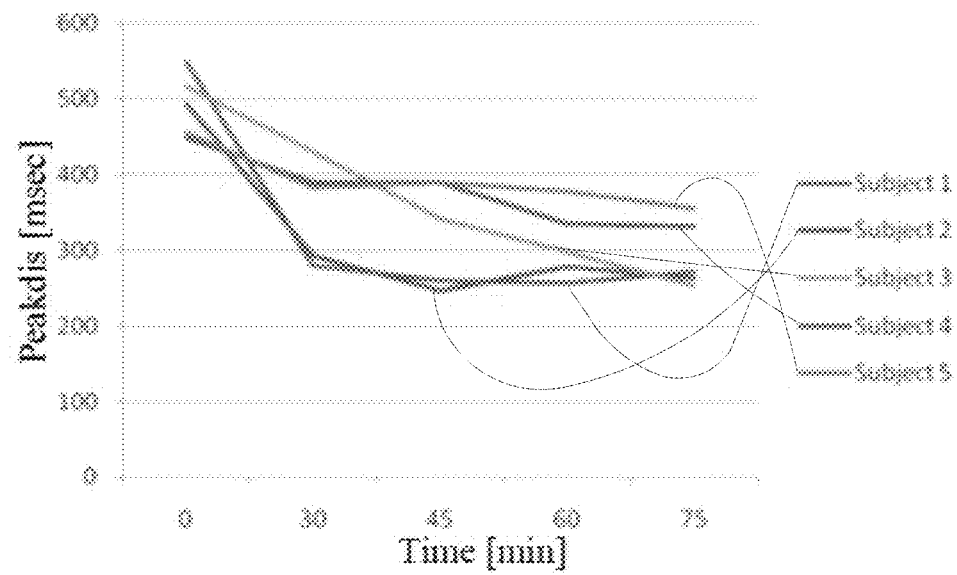

Referring to FIG. 16, the distance between peak polarities in a function describing the temporal variations of the position of the spatial correlation function's peak is illustrated. FIGS. 17a-17b are graphs illustrating the change of test subjects' distances between peak polarities over time, as a consequence of alcohol consumption.

The distance between peak polarities (also referred to as "peakdis") is the time in which the blood vessels moves from the maximum peak to the minimum peak or vice versa. This parameter is measured in milliseconds.

Table 10 summarizes values of the distance between peak polarities before drinking alcohol and after significant time (25 min & 35 min). Table 11 summarizes the values of the distance between peak polarities in the long duration test, where measurements were taken before drinking alcohol and every 15 min thereafter (for 75 min).

TABLE 10

|  | Before | After 25 min | After 35 min |
| --- | --- | --- | --- |
| subject 1 | 829.037 | 93.844 | 205.794 |
| subject 2 | 343.160 | 282.272 | 200.296 |
| subject 3 | 479.490 | 368.971 | — |
| subject 4 | 677.152 | 555.473 | — |
| subject 5 | 701.563 | 519.901 | 567.901 |
| reference | 643.062 | 644.170 |  |

TABLE 11

|  | 0 | 30 min | 45 min | 60 min | 75 min |
| --- | --- | --- | --- | --- | --- |
| subject 1 | 493.375 | 292.2 | 246.7273 | 277.7143 | 263.5714 |
| subject 2 | 548.7273 | 279.5833 | 258.8 | 256.6 | 271.4118 |
| subject 3 | 517.5333 | 429.1583 | 341.3083 | 298.4333 | 253.4583 |
| subject 4 | 448.2917 | 390.0658 | 390.0658 | 334.0167 | 332.0882 |
| subject 5 | 454.1429 | 383.625 | 390 | 378.5556 | 355.2174 |

The data of tables 10 and 11 is shown graphically in FIGS. 17a and 17b, respectively.

It can be seen that there is a prominent decrease in the time in which the blood vessel jumps from max peak to the minimum peak.

Figure 18:
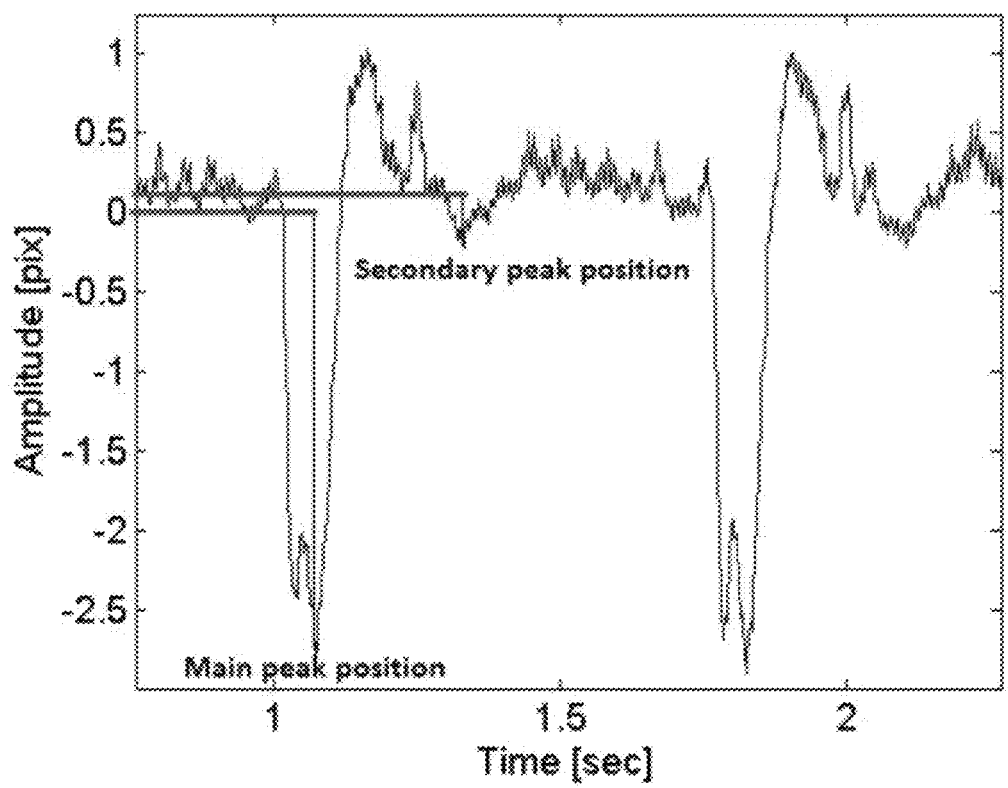
FIG. 18 is a graph illustrating the main and secondary peak positions in the function indicative of skin vibration profile in the time domain.
Figure 19A:
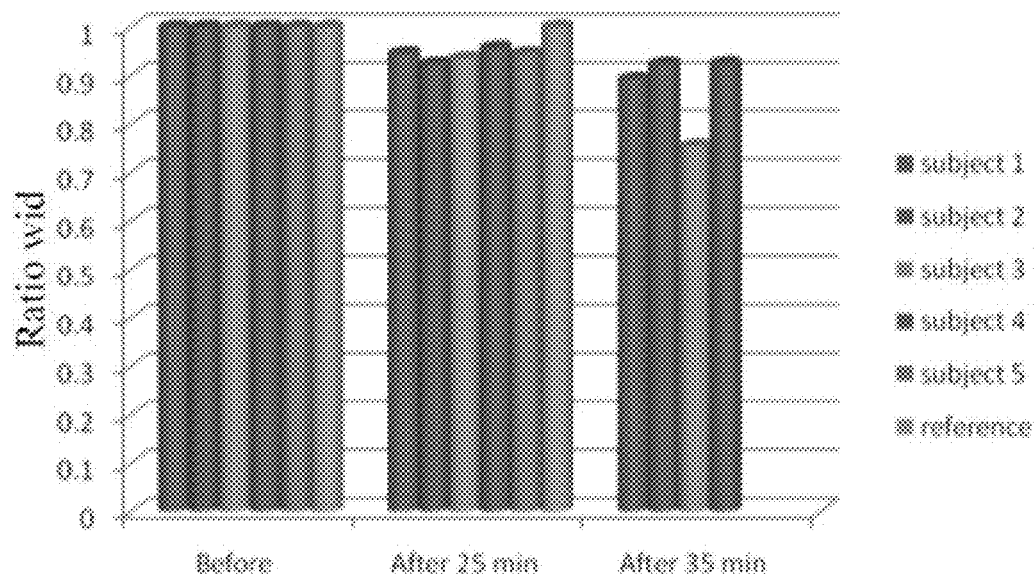
FIGS. 19a-19b are graphs illustrating the change of test subjects' ratios between main and secondary peak positions, as a consequence of alcohol consumption.
Figure 19B:
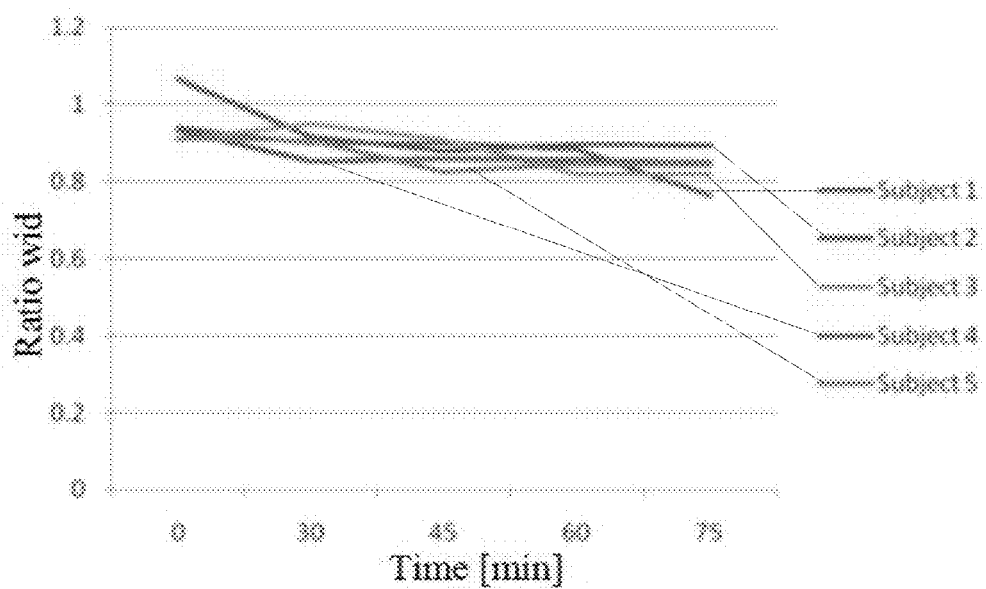

Referring to FIG. 18, the main and secondary peak positions in a function describing the temporal variations of the position of the peak of the spatial correlation function are shown. FIGS. 19a-19b are graphs illustrating the change of test subjects' ratios between main and secondary peak positions, as a consequence of alcohol consumption. The ratio between the main and the secondary peak position is without units.

Table 12 summarizes values of ratios between main and secondary peak positions before drinking alcohol and after significant time (25 min & 35 min). Table 13 summarizes the values of ratios between main and secondary peak positions in the long duration test, where measurements were taken before drinking alcohol and every 15 min thereafter (for 75 min). The data of tables 12 and 13 is shown graphically in FIGS. 19a and 19b, respectively.

TABLE 12

|  | Before | After 25 min | After 35 min |
| --- | --- | --- | --- |
| subject 1 | 0.93 | 0.88 | 0.83 |
| subject 2 | 0.93 | 0.86 | 0.86 |
| subject 3 | 0.94 | 0.88 | 0.71 |
| subject 4 | 0.94 | 0.90 | 0.87 |
| subject 5 | 0.92 | 0.87 | — |
| Reference | 0.90 |  | 0.91 |

TABLE 13

|  | 0 | 30 min | 45 min | 60 min | 75 min |
| --- | --- | --- | --- | --- | --- |
| subject 1 | 1.065769 | 0.916087 | 0.879866 | 0.89725 | 0.894333 |
| subject 2 | 0.940361 | 0.899331 | 0.899965 | 0.882474 | 0.762678 |
| subject 3 | 0.91134 | 0.950579 | 0.911402 | 0.818973 | 0.81925 |
| subject 4 | 0.932998 | 0.852055 | 0.860919 | 0.855898 | 0.84999 |
| subject 5 | 0.914711 | 0.906142 | 0.82784 | 0.844785 | 0.843547 |

Figure 20:
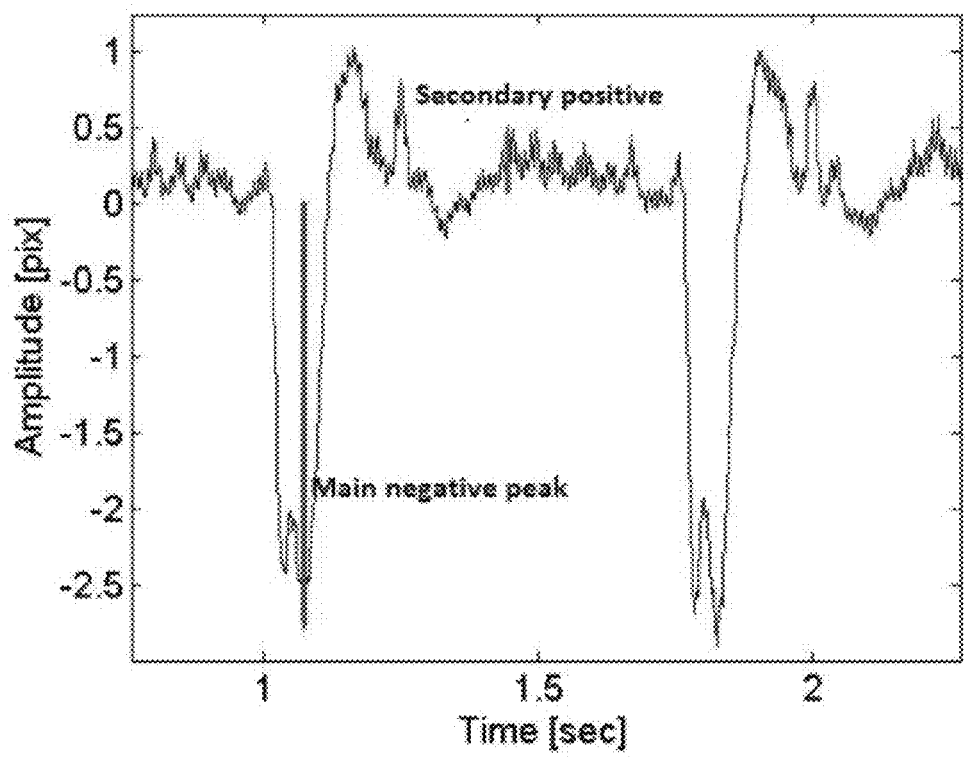
FIG. 20 is a graph illustrating the main negative peak amplitude to the secondary positive peak amplitude in the function indicative of skin vibration profile in the time domain.
Figure 21A:
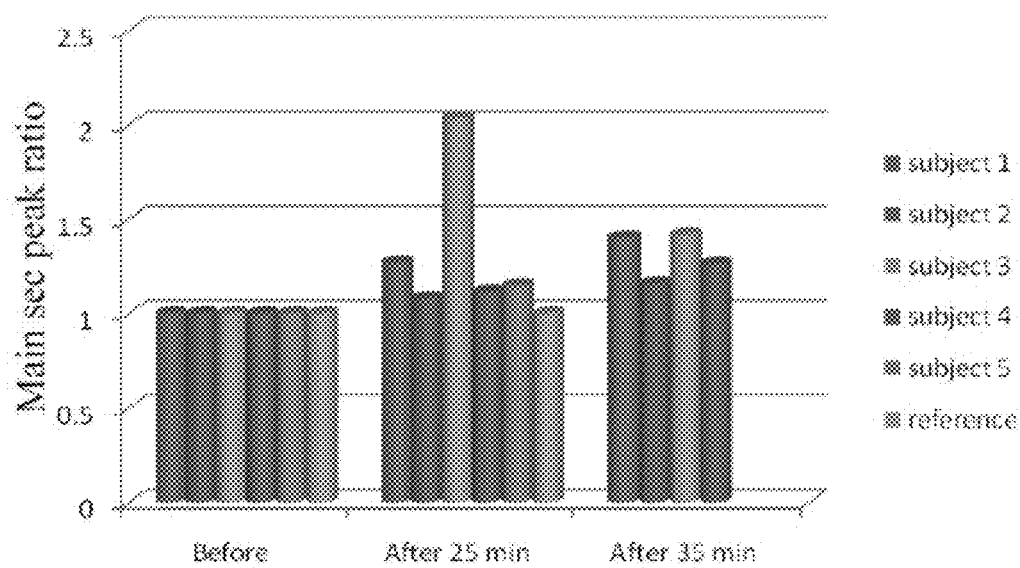
FIGS. 21a-21b are graphs illustrating the change of test subjects' ratios between main and secondary peak positions, as a consequence of alcohol consumption.
Figure 21B:
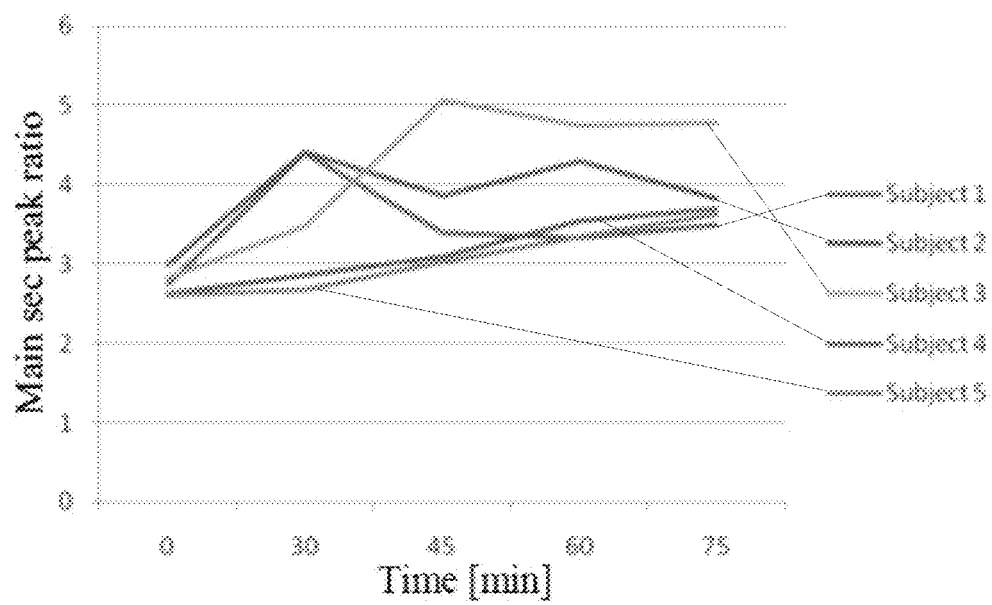

Referring to FIG. 20, the main negative peak amplitude and the secondary positive peak amplitude in a function describing the temporal variations of the position of the spatial correlation function's peak are shown. FIGS. 21a-21b are graphs illustrating the change of test subjects' ratios between main and secondary peak amplitudes, as a consequence of alcohol consumption.

Table 14 summarizes values of ratios between main and secondary peak amplitudes before drinking alcohol and after significant time (25 min & 35 min). Table 15 summarizes the values of ratios between main and secondary peak amplitudes in the long duration test, where measurements were taken before drinking alcohol and every 15 min thereafter (for 75 min). The data of tables 14 and 15 is shown graphically in FIGS. 21a and 21b, respectively.

TABLE 14

|  | Before | After 25 min | After 35 min |
| --- | --- | --- | --- |
| subject 1 | 3.38 | 4.30 | 4.74 |
| subject 2 | 2.60 | 2.81 | 3.02 |
| subject 3 | 1.90 | 3.87 | 2.70 |
| subject 4 | 1.73 | 1.93 | 2.19 |
| subject 5 | 2.26 | 2.60 | — |
| reference | 2.34 |  | 2.34 |

TABLE 15

|  | 0 | 30 min | 45 min | 60 min | 75 min |
| --- | --- | --- | --- | --- | --- |
| subject 1 | 2.997614 | 4.422284 | 3.86795 | 4.291934 | 3.837522 |
| subject 2 | 2.736866 | 4.403912 | 3.397398 | 3.323514 | 3.503098 |
| subject 3 | 2.834672 | 3.482034 | 5.07221 | 4.743223 | 4.78544 |
| subject 4 | 2.623532 | 2.858851 | 3.100125 | 3.539668 | 3.700689 |
| subject 5 | 2.611516 | 2.673833 | 3.034982 | 3.354123 | 3.633107 |

It can be seen that when there is an alcohol in the blood vessel, the secondary peak becomes smaller relative to the main pulse. This also demonstrates the importance of the behavior of the secondary pulse as an indicator of presence of alcohol in the blood vessels.

Figure 22:
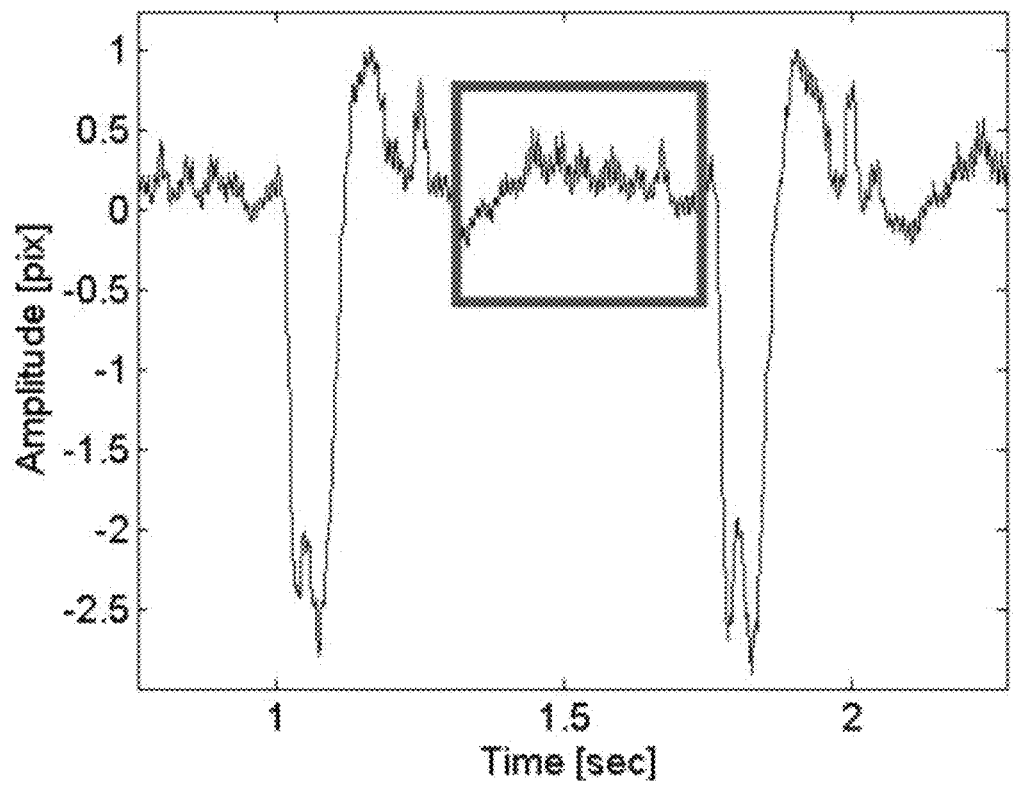
FIG. 22 is a graph illustrating the background noise in the function indicative of skin vibration profile in the time domain.
Figure 23:
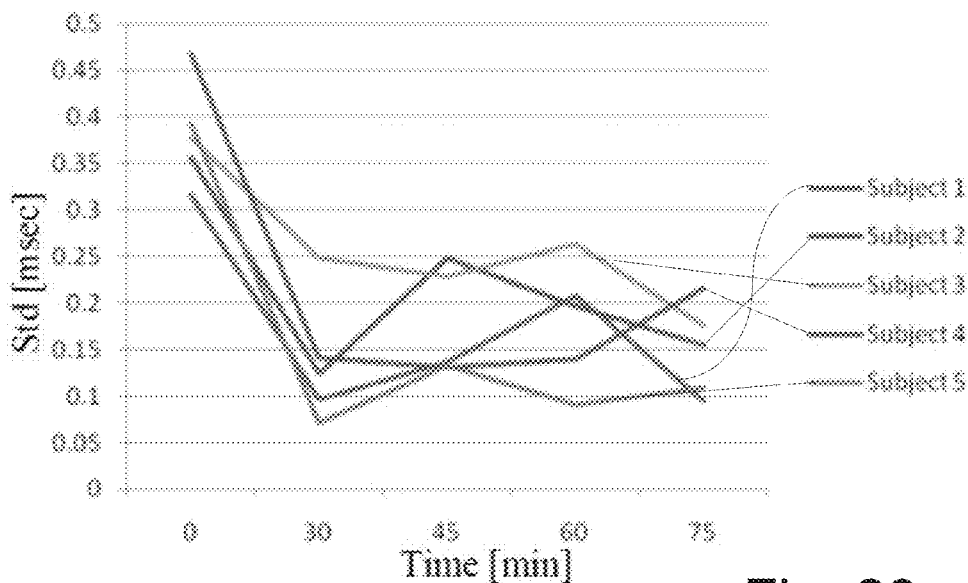
FIG. 23 is a graph illustrating the change of test subjects' standard deviation in background noise, as a consequence of alcohol consumption.

Referring to FIG. 22, the background noise in a function describing the temporal variations of the spatial position of the correlation function's peak indicative of skin vibration profile in the time domain is shown. FIG. 23 is a graph illustrating the change of test subjects' standard deviation of background noise, as a consequence of alcohol consumption.

The standard deviation of background noise, was checked only in the long duration tests.

Table 16 summarizes the values standard deviations of background noise in the long duration test, where measurements were taken before drinking alcohol and every 15 min thereafter (for 75 min). The data of table 16 is shown graphically in FIG. 23.

TABLE 16

|  | 0 | 30 min | 45 min | 60 min | 75 min |
| --- | --- | --- | --- | --- | --- |
| subject 1 | 0.3164 | 0.096496 | 0.137565 | 0.207878 | 0.095239 |
| subject 2 | 0.357475 | 0.12388 | 0.248033 | 0.19633 | 0.15489 |
| subject 3 | 0.378046 | 0.248033 | 0.228488 | 0.264168 | 0.175701 |
| subject 4 | 0.467773 | 0.140524 | 0.131381 | 0.140187 | 0.216425 |
| subject 5 | 0.392776 | 0.071516 | 0.132013 | 0.091129 | 0.109303 |

From table 16 and FIG. 23, it can be seen that when alcohol is present in the blood vessel, the background noise decreases.

Thus, it has been shown that the present invention can be also used for measuring alcohol level in the blood. The advantage provided by the technique of the present invention lies in the fact that the present technique enables real-time and non invasive estimation of alcohol in the bloodstream. This is in contrast with the known breath analysis technique, which is less reliable since it measures low concentrations of alcohol in breath.

Intra-Ocular Pressure

The following section, describing FIGS. 24-27, refers to tests conducted by the inventors on rabbits, in order to determine a relationship between intra-ocular pressure (IOP) and parameters of the vibration profile of the subjects' eye in the time domain.

The tests compared IOP of a rabbit's eye with the average amplitude of oscillations of a time-varying function describing the time varying position of the peak of the spatial correlation function (the time-varying function being indicative of vibrations of the rabbit's eye). The tests showed that the temporal change of the IOP is proportional to the temporal change of β(t) (which is proportional to the relative shift of the speckle pattern):

$$P_{IOP}(t) \propto \beta(t) \quad (10)$$

Therefore, β(t) can be used to estimate IOP.

The aim of the test was to show that the blood pressure in the blood vessels in the retina affects the movement of the sclera/iris in a way that is correlated to the IOP, i.e. the sclera/iris slightly pulsates due to the blood supply to the eye. This movement, although being very small, can be detected by the speckle-based measurement of the present invention, since the movement precision that our technique can allow is in the nanometric scale. It is important to emphasize that the measured movement is solely the pulse of the iris/sclera, and not the movements of the iris or the eye. The movements of the iris or the eye are undesirable, and can be we aim to filtered out by performing measurement over sufficiently short time scale.

In the experimental setup, rabbits had an infusion connected to their eye in order to control their IOP. The experimental system was set up as the system 200 of FIG. 2a, where and the optically based monitoring system was positioned at range of about 50 cm from the rabbit. The system included a fast camera and a laser. The readout of the camera was analyzed with Matlab software by a computer (control unit). The experimental system in monitored the secondary speckle patterns generated due to reflection from the rabbit's sclera, and tracked the trajectory of the movement of the speckle patterns. During the experiments the rabbits were anesthetized. The source of coherent light was a harmonic of CW Nd:YAG laser which produced a beam having wavelength of 532 nm to illuminate the sclera of the rabbit. The reflections were analyzed using fast digital camera from "PixeLink". The obtained results were analyzed with Matlab software.

In order to vary the IOP of the rabbit's eye during the experiment, the elevation of the infusion bag was changed. It is known that pressure difference is proportional to elevation difference and can be estimated as:

$$\Delta P = \rho g \Delta h \quad (11)$$

where $\rho$ is the density of the infusion liquid, g the gravity acceleration and $\Delta h$ the elevation difference. The translation between the pressure value obtained in Eq. 6 into mmHg units can be calculated using the following translation:

$$1 \text{ Pa} = 1 \text{ N/m}^2 = 9.8692 \times 10^{-6} \text{ atm} = 7.5006 \times 10^{-3} \text{ torr} = 7.5 \times 10^{-3} \text{ mmHg} \quad (12)$$

Figure 24:
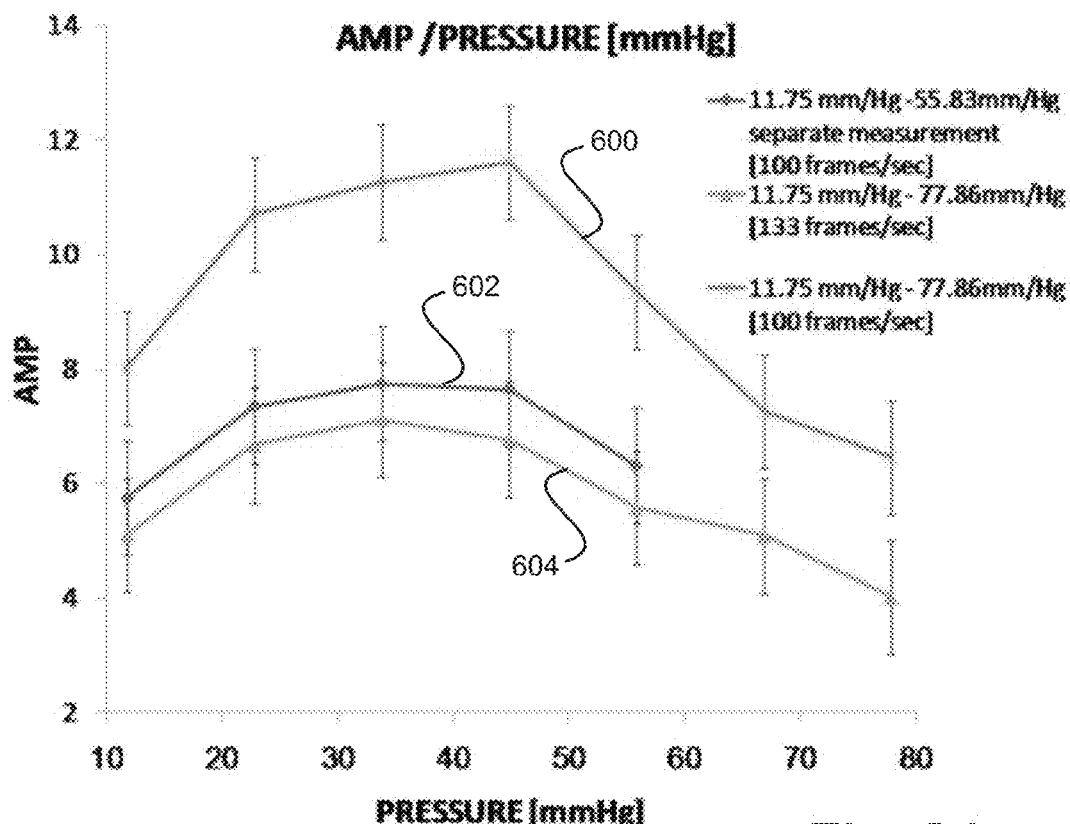
FIG. 24 is a graph illustrating the oscillation amplitude of a function indicative of the eye's vibration as a function of intra-ocular pressure (IOP), where the function was generated via the system of FIG. 2 using a 10 mW laser.

Referring to FIG. 24, there is depicted a graph illustrating the oscillation amplitude of a time-varying function describing the time varying position for the spatial correlation function's peak being indicative of the eye's vibration as a function of intra-ocular pressure (IOP), where the time varying-function was generated via the system of FIG. 2 using a 2 mW laser.

One may see the relation between the oscillation amplitude of the time varying position of the spatial correlation function's peak obtained by using the above mentioned experimental system and the IOP in mmHg units computed according to Eq. 6 and 7 (based on the height difference between the infusion bag and the eye of the rabbit).

The graph illustrates three different sets of measurements, each set being performed according to a different technique. The uppermost curve 600 was obtained by sampling at rate of 100 frames/sec, while each measurement was taken separately and not in a continuous manner along the time axis. The middle curve 602 corresponds to a measurement taken at sampling rate of 133 frames/sec in a continuous measuring manner. The lowermost curve 604 was obtained using a continuous measuring but at sampling rate of 100 frames/sec. The bars around each measurement designate the standard deviation that we had after averaging more than 20 measurements. The current to the laser was 0.2 A which means illumination power of about 2 mW.

From the obtained results one may see that the decrease in the optically determined oscillation amplitude of the time varying positions of the peak of the spatial correlation function is obtained for pressure above ~40 mmHg. This is since this was approximately the inherent IOP of the rabbit's eye; when pressure was induced above this IOP value, the decrease was measured since the infusion bag overcame the inherent pressure in the eye of the rabbit. One may also see that in the experiment, the error in measurement is about 15%. But it is important to note that the accuracy of conventional measurement devices is also about 10%-15% while the current technique is a remote non harmful measuring device.

Figure 25:
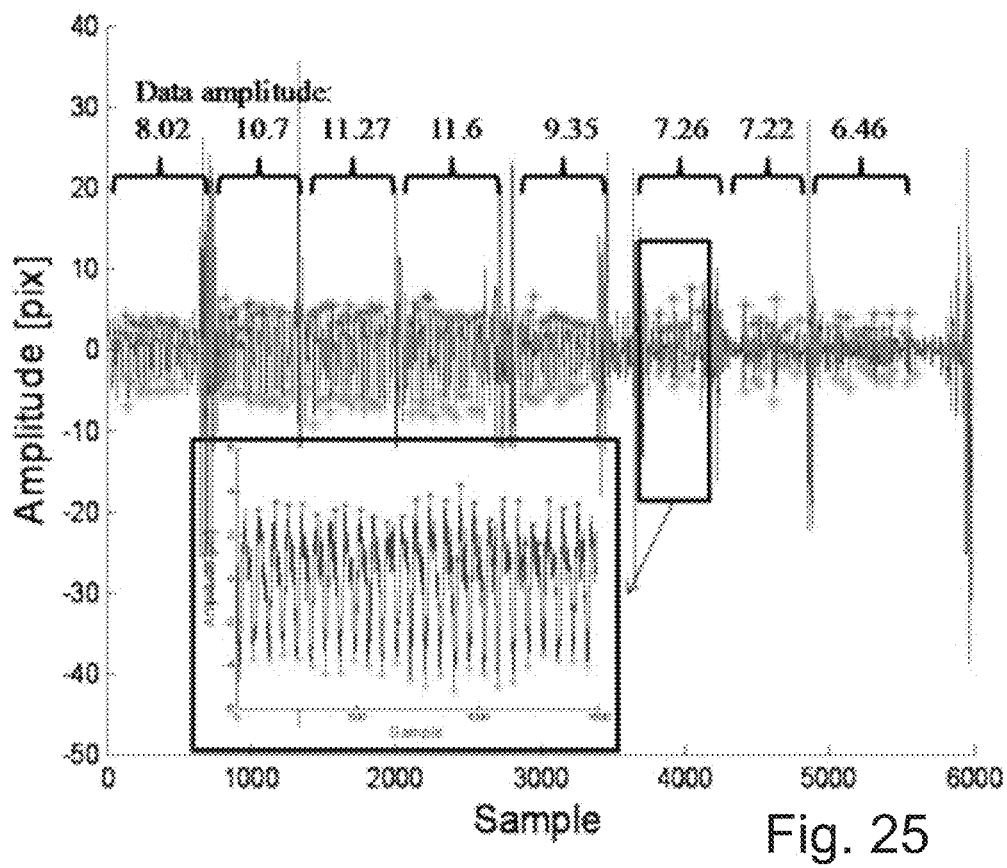
FIG. 25 is a graph illustrating a function indicative of the eye's vibration when IOP is changed in a rabbit's eye.

In order to understand how the values of the amplitude were extracted, reference is made to FIG. 25, which illustrates an example of the obtained readout in one of the performed experiments. In FIG. 25 one may see that a time-varying function describing the time varying position of the peak of the spatial correlation function being indicative of the eye's pulsating motion was generated. Every 500 samples, the elevation of the infusion bag was changed. During these changes, high amplitude artifacts appear due to the change in the elevation of the infusion bag. The oscillation amplitude of the time-varying function was measured and averaged for each set of 500 samples, in order to obtain an average amplitude corresponding to each elevation of the infusion bag (i.e. corresponding to a different IOP).

Figure 26:
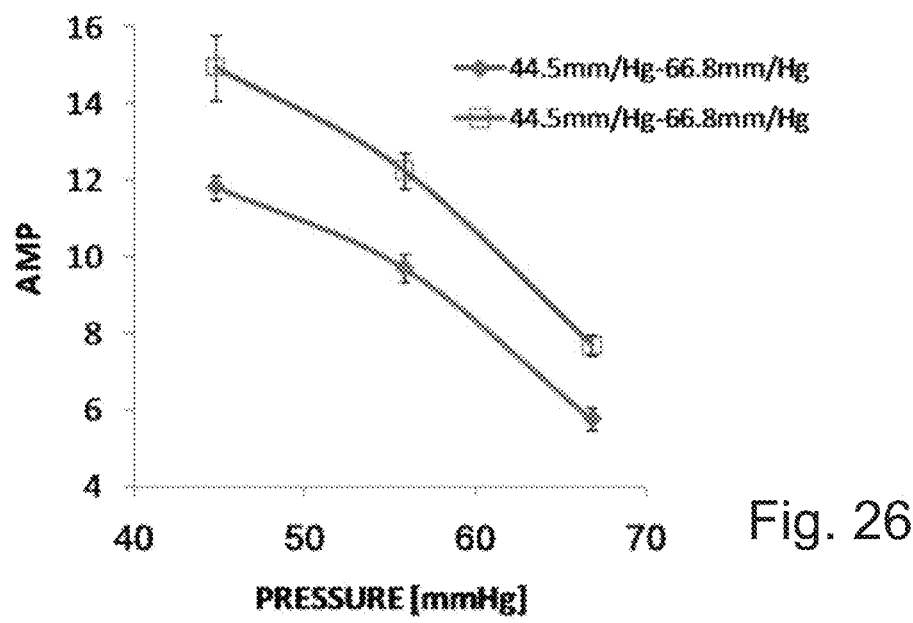
FIG. 26 is a graph illustrating amplitude of a function indicative of the eye's vibration as a function of intra-ocular pressure (IOP), where the function was generated via the system of FIG. 2 using a 2 mW laser.

The same experiment was repeated using a 10 mW laser. The results of this experiment are shown in FIG. 26. One may see that in this case the standard deviation error is much lower and can be estimated to be about 5%. The reason for the improved performance is related to the optical power of the illuminating laser. When the supply current was only 0.2 A the laser was at the threshold of its lasing and thus it was not stable enough. Its instability caused some of the standard deviations fluctuations. When the supply current was 0.25 A the laser was more stable and the results were much more repeatable. Note that the difference between the various curves in each one of the figures of FIGS. 24 and 26 is related to measurements performed at different positions along the sclera or measurements performed for different eyes. The standard variation for each one of the curves in FIGS. 24 and 26 is obtained for measurement performed in the same location for the same rabbit over the duration of the same experiment.

Note that the same measurement can be performed with eye-safe laser at wavelength of 1550 nm.

Figure 27:
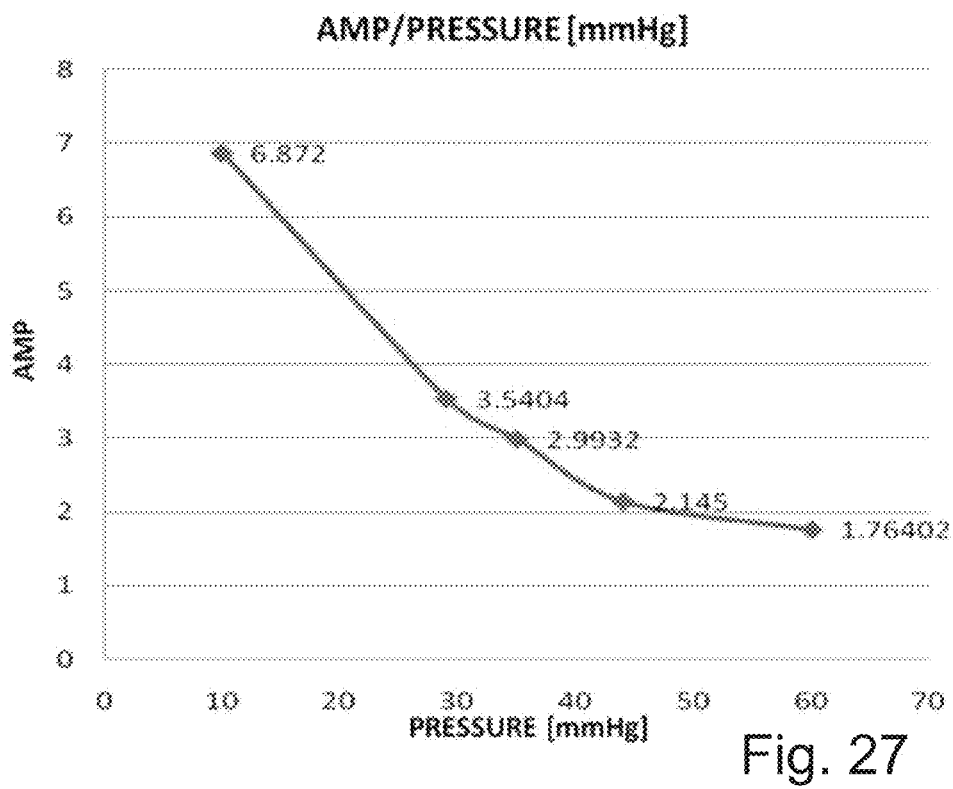
FIG. 27 is a graph illustrating the oscillation amplitude a function indicative of the eye's vibration as a function of intra-ocular pressure (IOP), where the IOP was measured via a Goldmann tonometer.

Referring to FIG. 27, there is depicted a graph illustrating the oscillation amplitude of time-varying function describing a time varying position of the peak of the spatial correlation function (the time-varying function being indicative of the eye's vibration) as a function of intra-ocular pressure (IOP), where the IOP was measured via a Goldmann tonometer.

Another important measurement was performed on a new rabbit following the same measurement procedure as for the experiment of FIG. 26, but this time the extracted results were compared with absolute reference measurement coming from a conventional Goldmann tonometer. The measurement was done as before by illuminating the rabbit's iris.

It must be noted that the measurement at 10 mm/Hg in FIG. 27 was performed before inserting the infusion bag. The measurement presented in FIGS. 24 and 26 were performed on rabbits after tens of attempts of inserting the infusion into their eye. Those attempts deformed the rabbit's eye and changed their inherent IOP. In the measurement of FIG. 27 a new rabbit was used and indeed its IOP was lower. In fact, it was verified, using the reference Goldmann tonometer, that the average IOP of the rabbits used in the experiments of FIGS. 24 and 26, that after finishing the experiment the rabbits' IOP indeed changed from 10 mmHg (before experiment) to around 35 mmHg (right after the experiment).

In FIG. 27, the extracted results show good monotonic relation between the optically measured amplitude and the reference IOP measurement. The amplitude values are smaller than those of FIGS. 24 and 26 since a lens with different focal length was used in the optical device (55 mm in FIG. 27 instead of a lens with focal length of 50 mm used to obtain the results of FIGS. 24 and 26).

From the obtained results included in FIG. 24, it can be seen that that the induced variations in the IOP causes a variation of the reflected speckle patterns at the iris of the rabbit's eye. In two of the experiments (uppermost curve 600 and lowermost curve 604), the monitoring of that variation was performed continuously, while in the third experiment (middle curve 602), the measurements were obtained independently one from each other. In all the three cases, the curve's tendency is the same and it validates the correlation existing between the IOP and the processing applied over the speckle patterns reflected from the iris.

When comparing the continuous monitoring experiments, both curves 600 and 604 have the same aspect but are scaled with respect to the global amplitude value. This is due to the fact that the lower the sampling rate, the lower is the amplitude of the speckle patterns.

In all the cases presented in FIG. 24, the measurement error has standard deviation of about 15%. The results depicted in FIG. 26 show a reduction of the standard deviation error until approximately 5%. The reason for that improved performance is related to the timing of the measurement. In fact, the results of FIG. 26 were obtained in the beginning stage of our experiment, while the results of FIG. 24 were obtained after large number of tests, which affected the structure and therefore also the IOP of the rabbit's eye. Note that the difference between the various curves of FIG. 24 and those of FIG. 26 arises either because the measurements were performed at different positions along the iris or because the measurements were performed on different eyes. The standard deviation for each one of the curves in FIGS. 24 and 26 is obtained for measurements performed in the same location for the same rabbit over the duration of the same experiment. This fact suggests that the standard deviation error may be independent of the measurement point.

The results presented in FIG. 27 show a monotonic and a distinct relation between the absolute reference measurement of the IOP performed by Goldmann tonometer and the amplitude readout produced by the constructed optical device.

The Goldmann tonometer has a measurement error of about 1 mmHg. In contrast, the error of the present technique, is about 0.775 mmHg—considering standard deviation error of 5% and a typical IOP values in humans of 15.5 mmHg in average. Therefore, the technique of the present invention provided both a lower measurement error (i.e. higher accuracy), as well as the advantage of remote and continuous monitoring capability.

Furthermore, increase in IOP is the major risk factor for glaucoma, while decrease in IOP indicates fluid leakage and deflation of the eyeball (an undesirable condition in its own right). The results of FIG. 24 show that the technique of the present invention is sensible to both increase and decrease of IOP.

Blood Pulse Pressure

As mentioned above, the technique of the present invention can be used to determine blood pulse pressure. To do this, a system similar to that of FIG. 2a can be used to illuminate a region of a patient's skin adjacent to blood vessel(s) (e.g. the wrist). Variations in the speckle pattern are detected and processed as described above to determine a correlation function and a time variation of a feature (e.g., peak position and/or peak size) of the correlation function. The time variation of the spatial correlation function has a profile similar to that shown as shown in FIG. 4, and the amplitude of the peaks is indicative of the blood flow in the measurement (illuminated) location. The inventors have found that the amplitude of the main peak (parameter 1 of FIG. 4) of the time varying spatial correlation function is in good correlation with the patient's blood pulse pressure, owing to the fact the time variation of the measured data (speckle pattern) corresponds to the blood flow (motion) within the measurement location.

Figure 28:
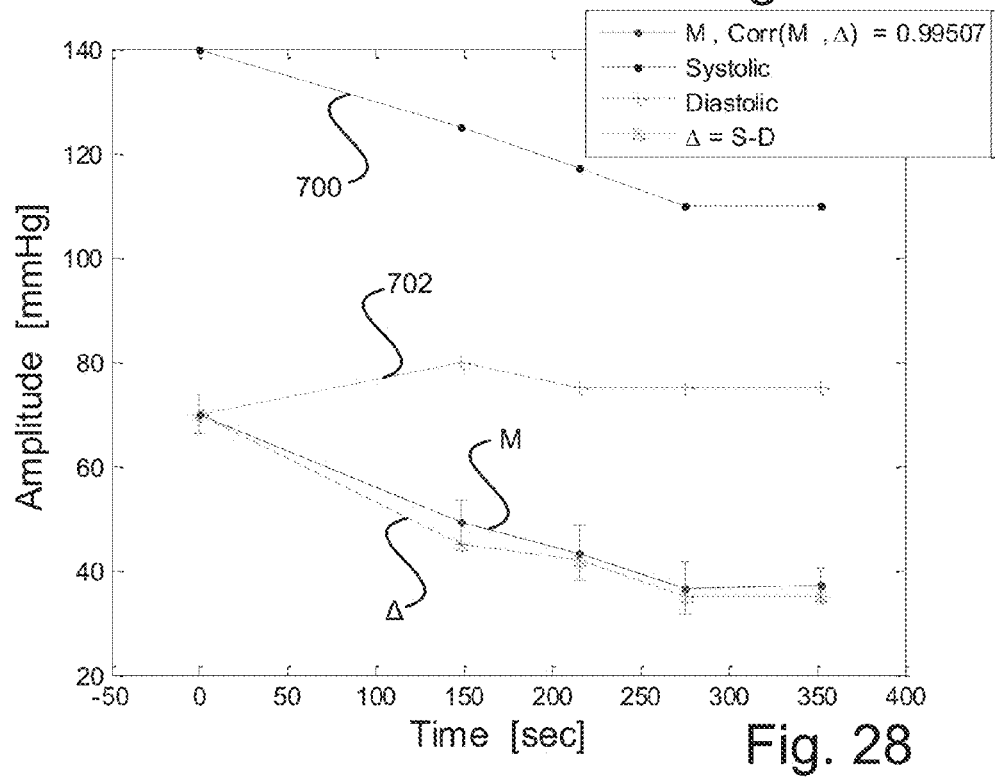
FIG. 28 is a graph illustrating the change of a test subject's pulse amplitude over time, as compared to the test subject's pulse blood pressure.

FIG. 28 is a graph illustrating the change of a test subject's pulse amplitude over time, as compared to the test subject's pulse blood pressure. The reference pulse pressure is shown by the curve denoted as curve Δ, and was obtained by subtracting diastolic pressure (curve 702) from systolic pressure (curve 700), both of which were measured using a manual sleeve-based reference measurement device. The curve (denoted as M) illustrates the value of the pulse amplitude obtained using the proposed optical technique at same time as the above-mentioned reference measurements. The time duration of the experiment was 350 sec. The sampling of the camera (PDA) was performed at 300 Hz. It can be seen that a strong correlation exists between the reference curve Δ and the curve M obtained by the technique of the present invention.

Dehydration:

The technique of the present invention can also be used to determine an amount of water in a biological tissue. To do this, a system similar to that of FIG. 2a can be used to illuminate the biological tissue (e.g. a portion of skin of a body). Variations in the speckle pattern are detected and processed as described above to determine a correlation function and a time variation of a feature (e.g., peak position and/or peak size) of the correlation function. Indeed, the amount of water in a tissue affects the movement profile of the surface of the tissue because it affects the flexibility and other mechanical properties of the tissue. Applying the opto-phone technology capable of monitoring movements with nanometric accuracy thereby allows (after proper calibration) to anticipate dehydration or even to estimate an amount of water in the tissue.

Coagulation of Blood (INR):

The technique of the present invention can also be used to determine a coagulation condition of blood. To do this, a system similar to that of FIG. 2a can be used to illuminate a portion of the skin. Variations in the speckle pattern are detected and processed as described above to determine a correlation function and a time variation of a feature (e.g., peak position and/or peak size) of the correlation function. Indeed, since a change in coagulation directly affects the viscosity of the blood, a change in coagulation strongly affects the mechanical movement of the surface of the skin that may be for example in proximity to a main blood artery. Measuring the movement profile with the opto phone may therefore allow after calibration to extract an INR parameter representing a coagulation condition of blood. The prothrombin time (PT) and its derived measures of prothrombin ratio (PR) and international normalized ratio (INR) are measures of the extrinsic pathway of coagulation. The result (in seconds) for a prothrombin time performed on a normal individual may vary according to the type of analytical system employed. This is due to the variations between different batches of manufacturer's tissue factor used in the reagent to perform the test. The INR was devised to standardize the results. Each manufacturer assigns an ISI value (International Sensitivity Index) for any tissue factor they manufacture. The ISI value indicates how a particular batch of tissue factor compares to an international reference tissue factor. The ISI is usually between 1.0 and 2.0. The INR is the ratio of a patient's prothrombin time (PT) to a normal (control) sample, raised to the power of the ISI value for the analytical system used.

$$INR = \left(\frac{PT_{test}}{PT_{normal}}\right)^{ISI}$$

Cattle Monitoring:

The technique of the present invention can also be used to determine biomedical parameters of a ruminant. Ruminant biomedical parameters monitoring such as monitoring of heart beating, pulse count, blood pulse pressure and breathing count can be very important in case of cattle as this information can be used to optimize the milking and the breeding timing of caws. Advantageously, such monitoring is performed without contact which is appreciable when dealing with animals. Applying the opto-phone technology and observing the surface of the skin of the caw, in positions that are close to a main blood artery, may allow—after monitoring of the movement and after proper calibration—to extract the above mentioned biomedical parameters in real time and in a continuous manner.

Temperature Monitoring:

The technique of the present invention can also be used to determine the temperature of a biological tissue. To do this, a system similar to that of FIG. 2a can be used to illuminate the biological tissue (e.g. a portion of skin of a body). Variations in the speckle pattern are detected and processed as described above to determine a correlation function and a time variation of a feature (e.g., peak position and/or peak size) of the correlation function. Indeed, the temperature of a tissue is related to the temporal movement profile of the tissue. Therefore, by extracting this profile and after proper calibration it is possible to estimate the temperature of the inspected tissue.

Flow Velocity and Volume Monitoring

The technique of the present invention can also be used to monitor the flow velocity and volume. The flow velocity and volume may be correlated to temporal variations of the spectral content of the temporal pattern of the correlation peak extracted from a correlation function between successive defocused images of a speckle pattern generated at a surface of an organ in which the flow is monitored. Indeed, by insetting nanoparticles through the flowing liquid and inspecting the temporal change in the speckle patterns generated due to the scattering from those nanoparticles, one may estimate the velocity and the volume of the flow because e.g. faster flow may generate faster movement of the speckle patterns. Thus, the velocity of flow is proportional to the temporal flickering of the inspected speckle patterns. This flickering can be computed in real time by correlation based processing.

The measurement of the opto phone provides sensing of the temporal movement profile of the inspected surface. It can be applied in plurality of wavelengths and in plurality of spatial positions. When plurality of wavelengths is applied, e.g. two, the measurements can be useful for application as oxymetry where the difference or the ratio of the temporal behavior at two wavelengths of absorption is inspected.

In case of flow velocity the measurement can be done in one of two possible ways. In a first method, measurement of the temporal profile may be simultaneously performed at two (or more) spatial positions with a known distance between them. By correlating the temporal sequence of pulses extracted from the two spatial positions, the temporal relative shift between the two sets of pulses may be computed. This temporal shift when dividing by the a priori known spatial distance between the two measurement points provides the flow velocity. In a second method, the measurement of the flow velocity can be done by doing only one measurement in a single spatial location. In this case the exact temporal profile of the pulsation is measured at high temporal resolution (with fast detector at sampling rate of e.g. GHz). Since the flow velocity affects the flow profile along the blood artery as explained above, the high precision extraction of the temporal pulsation profile can be related to the flow velocity. In all cases of measurement of the flow velocity and oxymetry etc, it is preferred to perform the measurement near principle blood artery where the pulsation affects are significantly more evident.

The invention claimed is:

1. A system for use in monitoring intra ocular pressure (IOP) of a subject's eye, the system comprising a control unit being a computer system comprising:

an input port which is in data communication with an external device and is configured and operable to receive input data from said external device, said input data being indicative of defocused coherent image data in the form of a sequence of speckle patterns collected from the eye with a certain sampling time pattern;

a processor configured and operable to carry out the following:

translate said defocused coherent image data into data comprising the IOP of the subject's eye, said translating comprising:

for each two successive speckle patterns in said sequence of the of speckle patterns, calculating a spatial correlation function having a correlation peak, and obtaining a sequence of spatial correlation functions, and transforming the sequence of the spatial correlation functions into a time varying spatial correlation function being a time-varying function of at least one spatial feature of a spatial correlation function between the successive speckle patterns in the sequence and being indicative of the change of the speckle pattern over time;

applying to said time varying spatial correlation function at least one predetermined model comprising model data indicative of a relation between one or more measurable parameters and one or more conditions of a subject's eye including the IOP condition, said applying to the function the at least one predetermined model comprising selecting at least one of the spatial features of the time-varying spatial correlation function indicative of an amplitude of oscillation of said function, and using said amplitude of oscillation as the measurable parameter to determine the IOP of the subject's eye; and generating output data indicative of said determined IOP of the subject's eye; and an output port configured to transmit said output data to at least one device configured to present the output data to a user, the output data comprising at least one of a graph of the time varying spatial correlation function and a value of the IOP condition being determined.

2. The system of claim 1, wherein the at least one selected spatial feature of the time-varying spatial correlation function describes a time varying position of a peak of the spatial correlation function.

3. The system of claim 1, wherein said certain sampling time pattern is selected to be of sufficiently short time scale, to enable filtering out speckle patterns associated with movements of subject's iris or eye, such that the speckle patterns in the collected defocused images correspond to pulses of sclera.

4. The system of claim 1, further comprising the external device comprising:

an imaging device comprising a coherent light source configured for illuminating a subject's eye with defocused illumination of a predetermined number of wavelengths according to the sampling time pattern during a sampling period, and a pixel detector array configured and operable for detecting the successive speckle patterns generated by the illuminated portion of the eye during the sampling period and generating said image data indicative of the sequence of the speckle patterns to be received by said input port of the control unit.

5. The system of claim 1, wherein said speckle patterns in the collected defocused images correspond to movement of aqueous humor in the eye.

6. The system of claim 1, wherein the oscillation amplitude of the time varying spatial correlation function is indicative of the eye's vibration as a function of the intraocular pressure (TOP) of the subject.

7. A system for use in monitoring intra ocular pressure (IOP) of a subject's eye, the system comprising a control unit being a computer system comprising:

an imaging device comprising a coherent light source configured for illuminating a subject's eye with defocused illumination of a predetermined number of wavelengths according to the sampling time pattern during a sampling period, and a pixel detector array configured and operable for detecting successive speckle patterns generated by the illuminated portion of the eye during the sampling period and generating image data indicative of the sequence of the speckle patterns; and a control unit configured and operable for data communication with the imaging device for receiving the image data, the control unit comprising a processor configured and operable to carry out the following:

translate said defocused coherent image data into data comprising the IOP of the subject's eye, said translating comprising: for each two successive speckle patterns in said sequence of the of speckle patterns, calculating a spatial correlation function having a correlation peak, and obtaining a sequence of spatial correlation functions; transforming the sequence of the spatial correlation functions into a time varying spatial correlation function being a time-varying function of at least one spatial feature of a spatial correlation function between the successive speckle patterns in the sequence and being indicative of the change of the speckle pattern over time; applying to said time varying spatial correlation function at least one predetermined model comprising model data indicative of a relation between one or more measurable parameters and one or more conditions of a subject's eye including the IOP condition, said applying to the function the at least one predetermined model comprising selecting at least one of the spatial features of the time-varying spatial correlation function indicative of an amplitude of oscillation of said function, and using said amplitude of oscillation as the measurable parameter to determine the IOP of the subject's eye; and generating output data indicative of said determined IOP of the subject's eye.

8. A method for use in monitoring intra ocular pressure (IOP) of a subject, the method being carried out by a computer system comprising a processor and a non-transitory computer readable memory and being configured for data communication with an external device, the method comprising:

receiving and storing, by the processor, input data from the external device, the input data being indicative of defocused coherent image data in the form of a sequence of speckle patterns collected from the eye with a certain sampling time pattern;

in response to said receiving of the image data, automatically processing, by the processor, the image data by executing computer-readable instructions stored in the non-transitory computer readable memory, the instructions causing the processor to perform carry out the following:

translate said defocused coherent image data into data comprising the IOP of the subject's eye, said translating comprising: for each two successive speckle patterns in said sequence of the of speckle patterns, calculating a spatial correlation function having a correlation peak, and obtaining a sequence of spatial correlation functions; transforming the sequence of the spatial correlation functions into a time varying spatial correlation function being a time-varying function of at least one spatial feature of a spatial correlation function between the successive speckle patterns in the sequence and being indicative of the change of the speckle pattern over time; applying to said time varying spatial correlation function at least one predetermined model comprising model data indicative of a relation between one or more measurable parameters and one or more conditions of a subject's eye including the IOP condition, said applying to the function the at least one predetermined model comprising selecting at least one of the spatial features of the time-varying spatial correlation function indicative of an amplitude of oscillation of said function, and using said amplitude of oscillation as the measurable parameter to determine the IOP of the subject's eye; and generate output data indicative of said determined IOP of the subject's eye, the output data comprising at least one of a graph of the time varying spatial correlation function and a value of the IOP condition being determined.

* * * * *